(12) United States Patent
Bovet et al.

(10) Patent No.: US 11,976,286 B2
(45) Date of Patent: May 7, 2024

(54) MODULATION OF NITRATE LEVELS IN PLANTS VIA MUTATION OF NITRATE REDUCTASE

(71) Applicant: PHILIP MORRIS PRODUCTS S.A., Neuchatel (CH)

(72) Inventors: Lucien Bovet, La Chaux-de-Fonds (CH); Prisca Campanoni, Villars-Burquin (CH); Simon Goepfert, Lausanne (CH)

(73) Assignee: Philip Morris Products S.A., Neuchatel (CH)

( * ) Notice: Subject to any disclaimer, the term of this patent is extended or adjusted under 35 U.S.C. 154(b) by 220 days.

(21) Appl. No.: 17/416,667

(22) PCT Filed: Dec. 16, 2019

(86) PCT No.: PCT/EP2019/085321
§ 371 (c)(1),
(2) Date: Jun. 21, 2021

(87) PCT Pub. No.: WO2020/141062
PCT Pub. Date: Jul. 9, 2020

(65) Prior Publication Data
US 2022/0186242 A1    Jun. 16, 2022

(30) Foreign Application Priority Data
Dec. 30, 2018  (EP) ..................................... 18215913

(51) Int. Cl.
C12N 15/82    (2006.01)
A24B 3/12    (2006.01)
(Continued)

(52) U.S. Cl.
CPC ............ *C12N 15/8243* (2013.01); *A24B 3/12* (2013.01); *A24B 15/10* (2013.01); *C12N 9/0044* (2013.01); *C12Y 107/01001* (2013.01)

(58) Field of Classification Search
None
See application file for complete search history.

(56) References Cited

U.S. PATENT DOCUMENTS

2017/0303582 A1* 10/2017 Lu et al. ............ C12N 15/8243

FOREIGN PATENT DOCUMENTS

WO    WO 2016/046288         3/2016
WO    WO-2016046288 A1 *    3/2016    ............... A01H 5/12

OTHER PUBLICATIONS

Zhao et al. "Over-Expression of a Tobacco Nitrate Reductase Gene in Wheat (*Triticum aestivum* L.) Increases Seed Protein Content and Weight without Augmenting Nitrogen Supplying" 2013 PLOS One 8(9):e74678 (11 total pages). (Year: 2013).*

(Continued)

*Primary Examiner* — Matthew R Keogh
*Assistant Examiner* — Rebecca Stephens
(74) *Attorney, Agent, or Firm* — Mueting Raasch Group

(57) ABSTRACT

A plant cell comprising: (a) a polynucleotide sequence encoding a nitrate reductase polypeptide comprising a contiguous polypeptide sequence of SEQ ID NO: 5 or SEQ ID NO: 7, wherein methionine is substituted for an amino acid that reduces nitrate reductase activity in the plant cell as compared to a control plant cell; (b) a polypeptide sequence encoded by the polynucleotide sequence set forth in (a); or (c) a construct, vector or expression vector comprising the polynucleotide sequence set forth in (b).

19 Claims, 3 Drawing Sheets
Specification includes a Sequence Listing.

(51) Int. Cl.
*A24B 15/10* (2006.01)
*C12N 9/06* (2006.01)

(56) References Cited

OTHER PUBLICATIONS

Lillo et al. "Mutation of the regulatory phosphorylation site of tobacco nitrate reductase results in constitutive activation of the enzyme in vivo and nitrite accumulation" 2003 Plant Journal 35: 566-573 . (Year: 2003).*
Hardin et al. "Coupling oxidative signals to protein phosphorylation via methionine oxidation in *Arabidopsis*" 2009 Biochem. J. 422: 305-312 . (Year: 2009).*
Campbell W.H., "Nitrate Reductase Structure, Function and Regulation: Bridging the Gap Between Biochemistry and Physiology," *Annu. Rev. Plant Physiol. Plant Mol. Biol.,* 50: 277-303, 1999.
Extended European Search Report for Application No. 18215913.7 dated Jun. 7, 2019 (8 pages).
Genbank Accession Number: National Center for Biotechnology Information, National Library of Medicine, National Institutes of Health, GenBank Locus X14059, Accession No. X14059, "Definition," Nicotiana Tabacum Nia-2 Gene for Nitrate Reductase (EC 1.6.6.1).
Genbank Accession Number: National Center for Biotechnology Information, National Library of Medicine, National Institutes of Health, GenBank Locus XP_023536153, Accession No. XP_023536153.1, "Definition," Nitrate Reductase [NADH]-like [Cucurbita Pepo Subsp. Pepo], Jan. 22, 2018, retrieved from the internet: URL: https://www.mcbi.nlm.nih.gov (retrieved on May 14, 2019).
Lillo et al., "Mechanism and Importance of Post-Translational Regulation of Nitrate Reductase", *Journal of Exp. Bot.,* 55(401): 1275-1282, 2004.
Lillo et al., "Mutation of the Regulatory Phosphorylation Site of Tobacco Nitrate Reductase Results in Constitutive Activation of the Enzyme in Vivo and Nitrite Accumulation,", *The Plant Journal* 35: 566-573, 2003.
PCT International Search Report and Written Opinion for Application No. PCT/EP2019/085321 dated Jan. 20, 2020 (10 pages).

* cited by examiner

E

F

SEQUENCE LISTING

```
<160> NUMBER OF SEQ ID NOS: 13

<210> SEQ ID NO 1
<211> LENGTH: 904
<212> TYPE: PRT
<213> ORGANISM: Nicotiana tabacum

<400> SEQUENCE: 1

Met Ala Ala Ser Val Glu Asn Arg Gln Phe Ser His Leu Glu Ala Gly
1               5                   10                  15

Leu Ser Arg Ser Phe Lys Pro Arg Ser Asp Ser Pro Val Arg Gly Cys
            20                  25                  30

Asn Phe Pro Ser Pro Asn Ser Thr Asn Phe Gln Lys Lys Pro Asn Ser
        35                  40                  45

Thr Ile Tyr Leu Asp Tyr Ser Ser Ser Glu Asp Asp Asp Asp Asp Asp
    50                  55                  60

Glu Lys Asn Glu Tyr Leu Gln Met Ile Lys Lys Gly Asn Ser Glu Leu
65                  70                  75                  80

Glu Pro Ser Val His Asp Thr Arg Asp Glu Gly Thr Ala Asp Asn Trp
                85                  90                  95

Ile Glu Arg Asn Phe Ser Met Ile Arg Leu Thr Gly Lys His Pro Phe
            100                 105                 110

Asn Ser Glu Pro Pro Leu Asn Arg Leu Met His His Gly Phe Ile Thr
        115                 120                 125

Pro Val Pro Leu His Tyr Val Arg Asn His Gly Pro Val Pro Lys Gly
    130                 135                 140
```

```
Thr Trp Asp Asp Trp Thr Val Glu Val Thr Gly Leu Val Lys Arg Pro
145                 150                 155                 160

Met Lys Phe Thr Met Asp Gln Leu Val Asn Glu Phe Pro Cys Arg Glu
            165                 170                 175

Leu Pro Val Thr Leu Val Cys Ala Gly Asn Arg Arg Lys Glu Gln Asn
        180                 185                 190

Met Val Lys Gln Thr Ile Gly Phe Asn Trp Gly Ala Ala Val Ser
        195                 200                 205

Thr Thr Ile Trp Arg Gly Val Pro Leu Arg Ala Leu Leu Lys Arg Cys
210                 215                 220

Gly Val Phe Ser Lys Asn Lys Gly Ala Leu Asn Val Cys Phe Glu Gly
225                 230                 235                 240

Ala Asp Val Leu Pro Gly Gly Gly Ser Lys Tyr Gly Thr Ser Ile
                245                 250                 255

Lys Lys Glu Phe Ala Met Asp Pro Ala Arg Asp Ile Ile Val Ala Tyr
            260                 265                 270

Met Gln Asn Gly Glu Lys Leu Ala Pro Asp His Gly Phe Pro Val Arg
            275                 280                 285

Met Ile Ile Pro Gly Phe Ile Gly Gly Arg Met Val Lys Trp Ile Lys
290                 295                 300

Arg Ile Ile Val Thr Thr Gln Glu Ser Asp Ser Tyr Tyr His Phe Lys
305                 310                 315                 320

Asp Asn Arg Val Leu Pro Pro His Val Asp Ala Glu Leu Ala Asn Thr
                325                 330                 335

Glu Ala Trp Trp Tyr Lys Pro Glu Tyr Ile Ile Asn Glu Leu Asn Ile
            340                 345                 350

Asn Ser Val Ile Thr Thr Pro Cys His Glu Glu Ile Leu Pro Ile Asn
            355                 360                 365

Ala Trp Thr Thr Gln Arg Pro Tyr Thr Leu Arg Gly Tyr Ser Tyr Ser
        370                 375                 380

Gly Gly Gly Lys Lys Val Thr Arg Val Glu Val Thr Leu Asp Gly Gly
385                 390                 395                 400

Glu Thr Trp Gln Val Ser Thr Leu Asp His Pro Glu Lys Pro Thr Lys
            405                 410                 415

Tyr Gly Lys Tyr Trp Cys Trp Cys Phe Trp Ser Leu Glu Val Glu Val
            420                 425                 430

Leu Asp Leu Leu Ser Ala Lys Glu Ile Ala Val Arg Ala Trp Asp Glu
        435                 440                 445

Thr Leu Asn Thr Gln Pro Glu Lys Leu Ile Trp Asn Val Met Gly Met
        450                 455                 460

Met Asn Asn Cys Trp Phe Arg Val Lys Met Asn Val Cys Lys Pro His
465                 470                 475                 480

Lys Gly Glu Ile Gly Ile Val Phe Glu His Pro Thr Gln Pro Gly Asn
            485                 490                 495

Gln Ser Gly Gly Trp Met Ala Lys Glu Arg His Leu Glu Ile Ser Ala
            500                 505                 510

Glu Ala Pro Gln Thr Leu Lys Lys Ser Ile Ser Thr Pro Phe Met Asn
        515                 520                 525

Thr Ala Ser Lys Met Tyr Ser Met Ser Glu Val Arg Lys His Ser Ser
        530                 535                 540

Ala Asp Ser Ala Trp Ile Ile Val His Gly His Ile Tyr Asp Ala Thr
545                 550                 555                 560
```

-continued

```
Arg Phe Leu Lys Asp His Pro Gly Gly Thr Asp Ser Ile Leu Ile Asn
            565                 570                 575
Ala Gly Thr Asp Cys Thr Glu Glu Phe Asp Ala Ile His Ser Asp Lys
        580                 585                 590
Ala Lys Lys Leu Leu Glu Asp Phe Arg Ile Gly Glu Leu Ile Thr Thr
    595                 600                 605
Gly Tyr Thr Ser Asp Ser Pro Gly Asn Ser Val His Gly Ser Ser Ser
610                 615                 620
Phe Ser Ser Phe Leu Ala Pro Ile Lys Glu Leu Val Pro Ala Gln Arg
625                 630                 635                 640
Ser Val Ala Leu Ile Pro Arg Glu Lys Ile Pro Cys Lys Leu Ile Asp
            645                 650                 655
Lys Gln Ser Ile Ser His Asp Val Arg Lys Phe Arg Phe Ala Leu Pro
        660                 665                 670
Ser Glu Asp Gln Val Leu Gly Leu Pro Val Gly Lys His Ile Phe Leu
    675                 680                 685
Cys Ala Val Ile Asp Asp Lys Leu Cys Met Arg Ala Tyr Thr Pro Thr
690                 695                 700
Ser Thr Ile Asp Glu Val Gly Tyr Phe Glu Leu Val Val Lys Ile Tyr
705                 710                 715                 720
Phe Lys Gly Ile His Pro Lys Phe Pro Asn Gly Gly Gln Met Ser Gln
            725                 730                 735
Tyr Leu Asp Ser Met Pro Leu Gly Ser Phe Leu Asp Val Lys Gly Pro
        740                 745                 750
Leu Gly His Ile Glu Tyr Gln Gly Lys Gly Asn Phe Leu Val His Gly
    755                 760                 765
Lys Gln Lys Phe Ala Lys Lys Leu Ala Met Ile Ala Gly Gly Thr Gly
770                 775                 780
Ile Thr Pro Val Tyr Gln Val Met Gln Ala Ile Leu Lys Asp Pro Glu
785                 790                 795                 800
Asp Asp Thr Glu Met Tyr Val Val Tyr Ala Asn Arg Thr Glu Asp Asp
            805                 810                 815
Ile Leu Leu Lys Glu Glu Leu Asp Ser Trp Ala Glu Lys Ile Pro Glu
        820                 825                 830
Arg Val Lys Val Trp Tyr Val Val Gln Asp Ser Ile Lys Glu Gly Trp
    835                 840                 845
Lys Tyr Ser Ile Gly Phe Ile Thr Glu Ala Ile Leu Arg Glu His Ile
850                 855                 860
Pro Glu Pro Ser His Thr Thr Leu Ala Leu Ala Cys Gly Pro Pro Pro
865                 870                 875                 880
Met Ile Gln Phe Ala Val Asn Pro Asn Leu Glu Lys Met Gly Tyr Asp
            885                 890                 895
Ile Lys Asp Ser Leu Leu Val Phe
            900
```

```
<210> SEQ ID NO 2
<211> LENGTH: 7096
<212> TYPE: DNA
<213> ORGANISM: Nicotiana tabacum

<400> SEQUENCE: 2
tacatacaag ggcgcgaata aactttttt aaagtaaatg tatatgaact tgcaatgaaa      60
gaggacctta acttgtttgt ctttgttgct ttctgcaaat ttcacctaa cagcccattt     120 gagattgatt tagttagtta taacaattag ttaaatgctt gtgtaatttg aagaaaatat    180
```

```
ttggacgtgc tcgctgaaaa cattatactc ctatataata gaaatacttt ctgaaaagtt      240
ggtcttgttc aaaaacgtat aagagagttg gtcttctcat aaatagtcac tagctttctg      300 atttttttc actttctata tcacgtaaat aggtactcaa atttgatatt tacaccaaac       360
aaatgaaaat aggatatgtg ttttcatac gtatatttat ctatcgtact taatgataca       420
tacatataca tataaccta cttttgatt actaaaaatt taattatatt taatttgggt       480
aaatatcaga tgccacaaaa catttaccta gccactgttt ttgactacta aaatttaat      540 tatgtttagc ttgggtaaat atcagatgtc actaaacatt ttacctagcc attcctccga      600
aaagaaattg agaaggaaat tagagttagt ggagccataa taatgtttaa tgtgaccata      660
actcggtgaa aaccacggca agaataagaa acagctgtta aggctaacca acagctgcat      720
atctttaagc catttgctat tacccaaca tcgcatcttc ctctgatccc gaccctacgg       780
gcgtaaaaag tgtaaatcgt tagaattgtt ttatttattt tatgatgtca ctatttttta      840 aaatcaaat taaattgggg tgtcgatttt tttgggtcct gcttatgtat agtatggcgc       900
tatggaggca ctgagagagt ccgaaacgtt tctatataag gccaccccac gcattcacaa      960
acttcgttcc caaacagaac aagaaaatca aatctcggag agagagagag agaaatattt     1020
tgagagagaa atacagaaaa tctctcttcc ttctttcctt ttttttcaa tccccattca     1080 tattcttttt ttagaataat ctatggcggc atctgtcgaa acaggcagt tcagtcacct      1140 agaagccggt ttatcccggt cttcaagcc ccggtctgat tccccggttc gtggctgcaa     1200
cttcccttcg cccaacagta ctaatttcca aaagaaacca aattccacca tttaccttga     1260
ttactcgtcg agtgaagacg acgatgatga tgacgaaaaa aatgagtacc ttcaaatgat     1320
taaaaagggg aattcagagt tagagccatc tgttcatgac actagggacg aaggtaccgc     1380
tgataattgg attgaacgca acttttccat gattcgtctc accggaaagc atccatttaa     1440
ctccgaacca ccgttgaacc ggctcatgca ccacggcttt atcacaccgg tcccacttca     1500
ttacgttcgt aaccatggac cggttcccaa gggcacgtgg gatgactgga ccgtggaagt     1560
cacgggacta gtgaagcgtc ctatgaaatt cacaatggac cagttggtta acgaattccc     1620
ttgtagagaa ttgcccgtta cgcttgtttg tgctggcaat cgaaggaaag aacagaacat     1680
ggttaaacaa accattggtt tcaactgggg cgccgctgcc gtttcaacaa cgatatggcg     1740
cggggtaccc ctccgcgctt tgctaaaacg gtgcggtgtt tttagcaaga ataaaggggc     1800
gcttaatgtt tgcttcgaag gagctgatgt gttgcccgga ggtggtggtt caaagtatgg     1860
aaccagcatt aagaaggaat ttgcaatgga tccagcacga gatatcatcg tagcctacat     1920
gcagaacgga gaaaaattgg cacccgacca cgggtttcca gtacgaatga taattccagg     1980
attcattgga ggaagaatgg tgaaatggat aaagaggatt atagtcacca cccaagaatc     2040
agacagctat tatcatttca aggacaatag agttcttcct ccccatgttg atgctgaact     2100
tgcaaatacc gaaggtacgt accgtaacta tttcaattta ttactccatt tgttccaatt     2160
tatgtgaacc tatttccttt ttggtccgtt caaaaagaa tgaaccttt ctaaatttgg      2220 taacaattta gcttaaactt acaacttcac ccttaatgag aaactttat aaccacacaa     2280 atacctggg gcccatttgg acttgtttag gtcgacaaat tccaaaagtt ttatttttt      2340 cttaaacttc gtgctcagtc aaacaggttc acgtaaattg aaacggagag agtatcattt     2400
ttattaaggg gtataaatat atttaatta gttgagactt gcacatacaa gtaaaatatt     2460
tcttagaata caaaatcaac tgaaagctta cttctaatta tatggttttg aattttcctt     2520
```

```
tcaatgaagt aaataaaaag gaaacaatta tattcaacgc atgtaggtat atggtcctgt      2580
cattatctca aatcaaatgg tttaaagaca aaggactttg gaaacataga attgtcagct      2640
ttatagttat ggagtactat attagttagc tgtttgcatc tattcataat tggtctatct      2700
gtgtgcagca tggtggtaca agccagagta tatcatcaat gagcttaata ttaactctgt      2760
cattacgacg ccgtgtcatg aagaaatttt gccaattaac gcctggacga ctcagcgacc      2820
ttacacgttg aggggctatt cttattctgg ttagtatttt tatattttcc gattttgctg      2880
agaatatcat atttcttagt tttgtcgata catcgtatcc tctaactctg acgttttact      2940
tcgtccttat gcacccactt acgtccttac tttctcagac agtttattga tgaaaactac      3000
ttactatttt cgacccgata gcctcagcgt ccttaattaa atgtgatgtt ttgaaagaga      3060
tattctctcc cgtctatttt aattaatttt tggctgtttt tatacgtggg aatctatttt      3120
taacattaat taatatagaa atgaaccata ttaatattat taatttcttc attgaaaata      3180
caacaaatac tcttcggctc ttactacaat gacaattttg aagaaaaata attaattcct      3240
tcctaatatc tgaaaaatca aatattgtgg accataaaaa aaggtcaaaa aattaattaa      3300
aatgaactgg agagagtaaa ttagaaaata taattatagc actagtaatt aaagttatta      3360
gatgtcttct ttaaaaagcg tgtgaaaact ttaaagacga aatataatat gaatattatc      3420
taatacttag aaagtgtcaa taattggtag acaatttaaa ctatatacta gttaaaaagt      3480
ctgtcaatac aactattagt attggggatt agagagaata gtagtaaaat ggagtaattg      3540
gacgcatgag cttgggcatg ctgattgctg tcagcttgtt tgctaatgtg aaaaagaaaa      3600
tagtaagaaa aggccaacat ggttttgttt atttttattat gtggtagtac acaaaaacct      3660
ggggagcttt cctagttctg aagagtcggt ctttggtagc acaaaattaa tagtatagta      3720
taccaagtga atattaaatt caattgtcta aagcacggaa tcttttttgac tactttagtt      3780 cctgcatctt gggttgcctc aacaacaccc tttattgaat tattatagta atgttcaata      3840
taatatacaa ttagaaaaca ctctaagtgg tcactttata tggatctagt caatactatt      3900
tcttctaaac aacgtgccta attacttccc actttccagt acatgaccac cattaagttt      3960
aatttttgtc aattccttgt gcaattggcc cttcaaatga gcagaagtgt tacgtaggaa      4020
aactaacttc agctactatt ataggagtaa acctgttagg aaaagatgct cgaggaactg      4080
acaaaacttg tagaataatt agccattgta ttgattgaaa tactgattgt gaacgtgtaa      4140
caaacaggcg gagggaaaaa agtaacgcga gtagaagtga cgttggatgg aggagaaaca      4200
tggcaagtta gcacactaga tcacccagag aagcccacca aatatggcaa gtactggtgt      4260
tggtgctttt ggtcactcga ggttgaggtg ttagacttgc tcagtgctaa agaaattgct      4320
gttcgagctt gggatgagac cctcaatact caacccgaga agcttatttg gaacgtcatg      4380
gtacgttcac ttcttctttt acctttattt cttttaactt ctatatacta gcggtgtaaa      4440
gttattttac accataagtt aacttacaaa aatatgtaac tatttatact acgagtgatg      4500
agggcaagaa ggggtttaag tatttgacaa taaatgtaaa ccctgcaatt tgttcctaa       4560 ttttttatcc tttcaactct ttgtgattgc ttcattatct agattcacag agcacatgtg      4620
ttcacatgcc aaaacaaaaa actacaaaca aaaaacttt tcactagctt tagtctaaga      4680
ttcccctttt tttttttggg aggtgtgtgg tccatactcc atagatcaat tccagccact      4740
gacgtaccaa accctgaaaa ttcctagtag ttatagcgac gtacaatcat ttcatattat      4800
gtaagcagag acgtgatcac atgaactaga tgtgaatacc acttgcccag tccaccaggt      4860
caattcatct agatgtgtaa atcttgacac cagcactggg tcacttttat aacactagca      4920
```

-continued

```
tttaacaaca tttcatcctt gaacattact tgggctaatt aataagtatt ttttttata    4980
tactctaaaa attgtaatta cataaatgaa tttaacttat acacgctgac aatgttacta    5040
attccacttt ttacggacgg ttatctatag aaatcattta ggtgaaacaa ttctcttaca    5100
ctatgatcag tgttagtaca taatggttat tacatttct aaatattgtg ctatgttgca    5160
atgttcaggg aatgatgaat aattgctggt tccgagtaaa gatgaatgtg tgcaagcctc    5220
acaagggaga gattggaata gtgtttgagc atccgactca acctggaaac caatcaggtg    5280
gatggatggc gaaggagaga catttggaga tatcagcaga ggcacctcaa acactaaaga    5340
agagtatctc aactccattc atgaacacag cttccaagat gtactccatg tccgaggtca    5400
ggaaacacag ctctgctgac tctgcttgga tcatagtcca tggtcatatc tatgacgcca    5460
cgcgtttctt gaaagatcac cctggtggga ctgacagcat tctcatcaat gctggcactg    5520
attgcactga ggaatttgat gcaattcatt ctgataaggc taagaagctc ttggaggatt    5580
tcaggattgg tgaactcata actactggtt acacctctga ctctcctggc aactccgtgc    5640
acggatcttc ttccttcagc agctttctag cacctattaa ggaacttgtt ccagcgcaga    5700
ggagtgtggc cctaattcca agagagaaaa tcccatgcaa actcatcgac aagcaatcca    5760
tctcccatga tgttaggaaa tttcgatttg cattgccctc tgaggatcaa gtcttgggct    5820
tgcctgttgg aaaacatatc ttcctctgtg ccgttattga cgataagctc tgcatgcgcg    5880
cttacacgcc tactagcacg atcgatgagg tggggtactt cgagttggtt gtcaagatat    5940
acttcaaagg aattcaccct aaattcccca atggagggca aatgtcacag tatcttgatt    6000
ctatgccgtt agggtcattt ctcgacgtga aggtccatt aggtcacatt gaataccaag    6060
gaaagggaaa ttcttagtt catggcaaac agaagtttgc caagaagttg gccatgatag    6120
caggtggaac aggaataact ccagtgtatc aagtcatgca ggcaattctg aaagatccag    6180
aagatgacac agaaatgtat gtggtgtatg ctaacagaac agaggatgat attttactta    6240
aggaagagct tgattcatgg gctgagaaaa ttccagagag ggttaaagtt tggtatgtgg    6300
ttcaggattc tattaaagaa ggatggaagt acagcattgg ttttattaca gaagccattt    6360
tgagagaaca tatccctgag ccatctcaca caacactggc tttggcttgt ggaccacctc    6420
ctatgattca atttgctgtt aatccaaact tggagaagat gggctatgac attaaggatt    6480
ccttattggt gttctaattt taaaaacaaa acaatatctg caggaataaa tttttttttt    6540
cccctatca gttgtacata ttgtatttgg tttatcaccc ccatgtacta cgtagtgttt    6600
gtagttctta catttttatt ttttagaatt ttttaaacc ttaggatata aaggttttct    6660
cttccaacaa agtgattctt tagggaagaa atgtactgta ctgtactagt atgtctaagc    6720
cgaaagttgt aatgtttacc atgacaaatt gtattcaatt cctcatggaa tagtaacatt    6780
gtgttcatgt gtcttcctgt aagcgatctt caaaatatca atgtatatat atagtaattg    6840
caaaccattg ttcctttcc cgatgtagtt aactactctt tctttagctt ctagtctctg    6900
gtgaatattt ttttttctat aactctttaa ttaatacggc cttaaataag agaaaagttt    6960
aaaccacgaa tatcattatg cagacgtata ggtaattaat ctacttttg aaaaaaatc    7020
tattttcttt atgtggtcct tcaaaataat attctagaac cttttgtata ttccctttta    7080
acttctattt agtttt                                                     7096
```

<210> SEQ ID NO 3
<211> LENGTH: 904
<212> TYPE: PRT

-continued

<213> ORGANISM: Nicotiana tabacum

<400> SEQUENCE: 3

Met Ala Ala Ser Val Glu Asn Arg Gln Phe Ser His Leu Glu Ala Gly
1               5                   10                  15

Leu Ser Arg Ser Phe Lys Pro Arg Ser Asp Ser Pro Val Arg Gly Cys
            20                  25                  30

Asn Phe Pro Ser Pro Asn Ser Thr Asn Phe Gln Lys Lys Pro Asn Ser
        35                  40                  45

Thr Ile Tyr Leu Asp Tyr Ser Ser Glu Asp Asp Asp Asp Asp
    50                  55                  60

Glu Lys Asn Glu Tyr Leu Gln Met Ile Lys Lys Gly Asn Ser Glu Leu
65                  70                  75                  80

Glu Pro Ser Val His Asp Thr Arg Asp Glu Gly Thr Ala Asp Asn Trp
                85                  90                  95

Ile Glu Arg Asn Phe Ser Met Ile Arg Leu Thr Gly Lys His Pro Phe
            100                 105                 110

Asn Ser Glu Pro Pro Leu Asn Arg Leu Met His His Gly Phe Ile Thr
        115                 120                 125

Pro Val Pro Leu His Tyr Val Arg Asn His Gly Pro Val Pro Lys Gly
    130                 135                 140

Thr Trp Asp Asp Trp Thr Val Glu Val Thr Gly Leu Val Lys Arg Pro
145                 150                 155                 160

Met Lys Phe Thr Met Asp Gln Leu Val Asn Glu Phe Pro Cys Arg Glu
                165                 170                 175

Leu Pro Val Thr Leu Val Cys Ala Gly Asn Arg Arg Lys Glu Gln Asn
            180                 185                 190

Met Val Lys Gln Thr Ile Gly Phe Asn Trp Gly Ala Ala Val Ser
        195                 200                 205

Thr Thr Ile Trp Arg Gly Val Pro Leu Arg Ala Leu Leu Lys Arg Cys
210                 215                 220

Gly Val Phe Ser Lys Asn Lys Gly Ala Leu Asn Val Cys Phe Glu Gly
225                 230                 235                 240

Ala Asp Val Leu Pro Gly Gly Gly Gly Ser Lys Tyr Gly Thr Ser Ile
                245                 250                 255

Lys Lys Glu Phe Ala Met Asp Pro Ala Arg Asp Ile Ile Val Ala Tyr
            260                 265                 270

Met Gln Asn Gly Glu Lys Leu Ala Pro Asp His Gly Phe Pro Val Arg
        275                 280                 285

Met Ile Ile Pro Gly Phe Ile Gly Gly Arg Met Val Lys Trp Ile Lys
    290                 295                 300

Arg Ile Ile Val Thr Thr Gln Glu Ser Asp Ser Tyr Tyr His Phe Lys
305                 310                 315                 320

Asp Asn Arg Val Leu Pro Pro His Val Asp Ala Glu Leu Ala Asn Thr
                325                 330                 335

Glu Ala Trp Trp Tyr Lys Pro Glu Tyr Ile Ile Asn Glu Leu Asn Ile
            340                 345                 350

Asn Ser Val Ile Thr Thr Pro Cys His Glu Glu Ile Leu Pro Ile Asn
        355                 360                 365

Ala Trp Thr Thr Gln Arg Pro Tyr Thr Leu Arg Gly Tyr Ser Tyr Ser
    370                 375                 380

Gly Gly Gly Lys Lys Val Thr Arg Val Glu Val Thr Leu Asp Gly Gly
385                 390                 395                 400

```
Glu Thr Trp Gln Val Ser Thr Leu Asp His Pro Glu Lys Pro Thr Lys
                    405                 410                 415

Tyr Gly Lys Tyr Trp Cys Trp Cys Phe Trp Ser Leu Glu Val Glu Val
            420                 425                 430

Leu Asp Leu Leu Ser Ala Lys Glu Ile Ala Val Arg Ala Trp Asp Glu
                435                 440                 445

Thr Leu Asn Thr Gln Pro Glu Lys Leu Ile Trp Asn Val Met Gly Met
    450                 455                 460

Met Asn Asn Cys Trp Phe Arg Val Lys Met Asn Val Cys Lys Pro His
465                 470                 475                 480

Lys Gly Glu Ile Gly Ile Val Phe Glu His Pro Thr Gln Pro Gly Asn
                485                 490                 495

Gln Ser Gly Gly Trp Met Ala Lys Glu Arg His Leu Glu Ile Ser Ala
            500                 505                 510

Glu Ala Pro Gln Thr Leu Lys Lys Ser Ile Ser Thr Pro Phe Ile Asn
            515                 520                 525

Thr Ala Ser Lys Met Tyr Ser Met Ser Glu Val Arg Lys His Ser Ser
    530                 535                 540

Ala Asp Ser Ala Trp Ile Ile Val His Gly His Ile Tyr Asp Ala Thr
545                 550                 555                 560

Arg Phe Leu Lys Asp His Pro Gly Gly Thr Asp Ser Ile Leu Ile Asn
                565                 570                 575

Ala Gly Thr Asp Cys Thr Glu Glu Phe Asp Ala Ile His Ser Asp Lys
            580                 585                 590

Ala Lys Lys Leu Leu Glu Asp Phe Arg Ile Gly Glu Leu Ile Thr Thr
            595                 600                 605

Gly Tyr Thr Ser Asp Ser Pro Gly Asn Ser Val His Gly Ser Ser Ser
    610                 615                 620

Phe Ser Ser Phe Leu Ala Pro Ile Lys Glu Leu Val Pro Ala Gln Arg
625                 630                 635                 640

Ser Val Ala Leu Ile Pro Arg Glu Lys Ile Pro Cys Lys Leu Ile Asp
                645                 650                 655

Lys Gln Ser Ile Ser His Asp Val Arg Lys Phe Arg Phe Ala Leu Pro
            660                 665                 670

Ser Glu Asp Gln Val Leu Gly Leu Pro Val Gly Lys His Ile Phe Leu
            675                 680                 685

Cys Ala Val Ile Asp Asp Lys Leu Cys Met Arg Ala Tyr Thr Pro Thr
    690                 695                 700

Ser Thr Ile Asp Glu Val Gly Tyr Phe Glu Leu Val Val Lys Ile Tyr
705                 710                 715                 720

Phe Lys Gly Ile His Pro Lys Phe Pro Asn Gly Gly Gln Met Ser Gln
                725                 730                 735

Tyr Leu Asp Ser Met Pro Leu Gly Ser Phe Leu Asp Val Lys Gly Pro
            740                 745                 750

Leu Gly His Ile Glu Tyr Gln Gly Lys Gly Asn Phe Leu Val His Gly
            755                 760                 765

Lys Gln Lys Phe Ala Lys Lys Leu Ala Met Ile Ala Gly Gly Thr Gly
    770                 775                 780

Ile Thr Pro Val Tyr Gln Val Met Gln Ala Ile Leu Lys Asp Pro Glu
785                 790                 795                 800

Asp Asp Thr Glu Met Tyr Val Val Tyr Ala Asn Arg Thr Glu Asp Asp
                805                 810                 815

Ile Leu Leu Lys Glu Glu Leu Asp Ser Trp Ala Glu Lys Ile Pro Glu
```

```
              820                 825                 830
Arg Val Lys Val Trp Tyr Val Val Gln Asp Ser Ile Lys Glu Gly Trp
              835                 840                 845
Lys Tyr Ser Ile Gly Phe Ile Thr Glu Ala Ile Leu Arg Glu His Ile
              850                 855                 860
Pro Glu Pro Ser His Thr Thr Leu Ala Leu Ala Cys Gly Pro Pro Pro
865                 870                 875                 880
Met Ile Gln Phe Ala Val Asn Pro Asn Leu Glu Lys Met Gly Tyr Asp
              885                 890                 895
Ile Lys Asp Ser Leu Leu Val Phe
              900

<210> SEQ ID NO 4
<211> LENGTH: 7096
<212> TYPE: DNA
<213> ORGANISM: Nicotiana tabacum

<400> SEQUENCE: 4
tacatacaag ggcgcgaata aacttttttt aaagtaaatg tatatgaact tgcaatgaaa      60
gaggacctta acttgtttgt ctttgttgct ttctgcaaat ttcaccttaa cagcccattt     120
gagattgatt tagttagtta taacaattag ttaaatgctt gtgtaatttg aagaaaatat     180
ttggacgtgc tcgctgaaaa cattatactc tatataata gaaatacttt ctgaaaagtt     240
ggtcttgttc aaaaacgtat aagagagttg gtcttctcat aaatagtcac tagctttctg     300
attttttttc actttctata tcacgtaaat aggtactcaa atttgatatt tacaccaaac     360
aaatgaaaat aggatatgtg ttttttcatac gtatatttat ctatcgtact taatgataca     420
tacatataca tataacccta cttttttgatt actaaaaatt taattatatt taatttgggt     480
aaatatcaga tgccacaaaa catttaccta gccactgttt ttgactacta aaaatttaat     540
tatgtttagc ttgggtaaat atcagatgtc actaaacatt ttacctagcc attcctccga     600
aaagaaattg agaaggaaat tagagttagt ggagccataa taatgtttaa tgtgaccata     660
actcggtgaa aaccacggca agaataagaa acagctgtta aggctaacca acagctgcat     720
atctttaagc catttgctat taccccaaca tcgcatcttc ctctgatccc gaccctacgg     780
gcgtaaaaag tgtaaatcgt tagaattgtt ttatttattt tatgatgtca ctattttta     840
aaatcaaaat taaattgggg tgtcgatttt tttgggtcct gcttatgtat agtatggcgc     900
tatggaggca ctgagagagt ccgaaacgtt tctatataag gccacccccac gcattcacaa     960
acttcgttcc caaacagaac aagaaaatca aatctcggag agagagagag agaaatattt    1020
tgagagagaa atacagaaaa tctctcttcc ttctttcctt ttttttttcaa tccccattca    1080
tattctttt ttagaataat ctatggcggc atctgtcgaa acaggcagt tcagtcacct    1140
agaagccggt ttatcccggt ctttcaagcc ccggtctgat tccccggttc gtggctgcaa    1200
cttcccttcg cccaacagta ctaatttcca aagaaaacca aattccacca tttaccttga    1260
ttactcgtcg agtgaagacg acgatgatga tgacgaaaaa aatgagtacc ttcaaatgat    1320
taaaaaaggg aattcagagt tagagccatc tgttcatgac actagggacg aaggtaccgc    1380
tgataattgg attgaacgca acttttccat gattcgtctc accggaaagc atccatttaa    1440
ctccgaacca ccgttgaacc ggctcatgca ccacggcttt atcacaccgg tcccacttca    1500
ttacgttcgt aaccatggac cggttcccaa gggcacgtgg gatgactgga ccgtggaagt    1560
cacgggacta gtgaagcgtc ctatgaaatt cacaatggac cagttggtta acgaattccc    1620
```

```
ttgtagagaa ttgcccgtta cgcttgtttg tgctggcaat cgaaggaaag aacagaacat    1680
ggttaaacaa accattggtt tcaactgggg cgccgctgcc gtttcaacaa cgatatggcg    1740
cggggtaccc ctccgcgctt tgctaaaacg gtgcggtgtt tttagcaaga ataaaggggc    1800
gcttaatgtt tgcttcgaag gagctgatgt gttgcccgga ggtggtggtt caaagtatgg    1860
aaccagcatt aagaaggaat tgcaatggga tccagcacga gatatcatcg tagcctacat    1920
gcagaacgga gaaaaattgg cacccgacca cgggtttcca gtacgaatga taattccagg    1980
attcattgga ggaagaatgg tgaaatggat aaagaggatt atagtcacca cccaagaatc    2040
agacagctat tatcatttca aggacaatag agttcttcct ccccatgttg atgctgaact    2100
tgcaaatacc gaaggtacgt accgtaacta tttcaattta ttactccatt tgttccaatt    2160
tatgtgaacc tatttccttt ttggtccgtt caaaaaagaa tgaaccctt ctaaatttgg    2220 taacaattta gcttaaactt acaacttcac ccttaatgag aaactttat aaccacacaa     2280 ataccctggg gcccatttgg acttgtttag gtcgacaaat tccaaaagtt ttattttttt    2340
cttaaacttc gtgctcagtc aaacaggttc acgtaaattg aaacggagag agtatcattt    2400
ttattaaggg gtataaatat attttaatta gttgagactt gcacatacaa gtaaaatatt    2460
tcttagaata caaaatcaac tgaaagctta cttctaatta tatggttttg aattttcctt    2520
tcaatgaagt aaataaaaag gaaacaatta tattcaacgc atgtaggtat atggtcctgt    2580
cattatctca aatcaaatgg tttaaagaca aaggactttg gaaacataga attgtcagct    2640
ttatagttat ggagtactat attagttagc tgtttgcatc tattcataat tggtctatct    2700
gtgtgcagca tggtggtaca agccagagta tatcatcaat gagcttaata ttaactctgt    2760
cattacgacg ccgtgtcatg aagaaatttt gccaattaac gcctggacga ctcagcgacc    2820
ttacacgttg aggggctatt cttattctgg ttagtatttt tatatttcc gattttgctg    2880 agaatatcat atttcttagt tttgtcgata catcgtatcc tctaactctg acgttttact    2940 tcgtcccttat gcacccactt acgtcctac tttctcagac agtttattga tgaaaactac    3000
ttactatttt cgacccgata gcctcagcgt ccttaattaa atgtgatgtt tgaaagaga    3060 tattctctcc cgtctatttt aattaatttt tggctgtttt tatacgtggg aatctatttt    3120
taacattaat taatatagaa atgaaccata ttaatattat taatttcttc attgaaaata    3180
caacaaatac tcttcggctc ttactacaat gacaattttg aagaaaaata attaattcct    3240
tcctaatatc tgaaaaatca atattgtgg accataaaaa aaggtcaaaa aattaattaa     3300
aatgaactgg agagagtaaa ttagaaaata taattatagc actagtaatt aaagttatta    3360
gatgtcttct ttaaaaagcg tgtgaaaact ttaaagacga aatataatat gaatattatc    3420
taatacttag aaagtgtcaa taattggtag acaatttaaa ctatatacta gttaaaaagt    3480
ctgtcaatac aactattagt attggggatt agagagaata gtagtaaaat ggagtaattg    3540
gacgcatgag cttgggcatg ctgattgctg tcagcttgtt tgctaatgtg aaaagaaaa    3600 tagtaagaaa aggccaacat ggttttgttt attttattat gtggtagtac acaaaaacct    3660
ggggagcttt cctagttctg aagagtcggt ctttggtagc acaaaattaa tagtatagta    3720
taccaagtga atattaaatt caattgtcta agcacggaa tcttttttgac tactttagtt     3780 cctgcatctt gggttgcctc aacaacaccc tttattgaat tattatagta atgttcaata    3840
taatatacaa ttagaaaaca ctctaagtgg tcactttata tggatctagt caatactatt    3900
tcttctaaac aacgtgccta attacttccc actttccagt acatgaccac cattaagttt    3960 aattttttgtc aattccttgt gcaattggcc cttcaaatga gcagaagtgt tacgtaggaa    4020
```

```
aactaacttc agctactatt ataggagtaa acctgttagg aaaagatgct cgaggaactg    4080
acaaaacttg tagaataatt agccattgta ttgattgaaa tactgattgt gaacgtgtaa    4140
caaacaggcg gagggaaaaa agtaacgcga gtagaagtga cgttggatgg aggagaaaca    4200
tggcaagtta gcacactaga tcacccagag aagcccacca aatatggcaa gtactggtgt    4260
tggtgctttt ggtcactcga ggttgaggtg ttagacttgc tcagtgctaa agaaattgct    4320
gttcgagctt gggatgagac cctcaatact caacccgaga agcttatttg gaacgtcatg    4380
gtacgttcac ttcttctttt acctttattt cttttaactt ctatatacta gcggtgtaaa    4440
gttattttac accataagtt aacttacaaa aatatgtaac tatttatact acgagtgatg    4500
agggcaagaa ggggtttaag tatttgacaa taaatgtaaa ccctgcaatt ttgttcctaa    4560 tttttttatcc tttcaactct ttgtgattgc ttcattatct agattcacag agcacatgtg    4620
ttcacatgcc aaaacaaaaa actacaaaca aaaaacttt tcactagctt tagtctaaga    4680
ttcccctttt tttttttggg aggtgtgtgg tccatactcc atagatcaat tccagccact    4740
gacgtaccaa accctgaaaa ttcctagtag ttatagcgac gtacaatcat ttcatattat    4800
gtaagcagag acgtgatcac atgaactaga tgtgaatacc acttgcccag tccaccaggt    4860
caattcatct agatgtgtaa atcttgacac cagcactggg tcacttttat aacactagca    4920
tttaacaaca tttcatcctt gaacattact tgggctaatt aataagtatt ttttttata     4980 tactctaaaa attgtaatta cataaatgaa tttaacttat acacgctgac aatgttacta    5040
attccacttt ttacggacgg ttatctatag aaatcattta ggtgaaacaa ttctcttaca    5100
ctatgatcag tgttagtaca taatggttat tacattttct aaatattgtg ctatgttgca    5160
atgttcaggg aatgatgaat aattgctggt tccgagtaaa gatgaatgtg tgcaagcctc    5220
acaagggaga gattggaata gtgtttgagc atccgactca acctggaaac caatcaggtg    5280
gatggatggc gaaggagaga catttggaga tatcagcaga ggcacctcaa acactaaaga    5340
agagtatctc aactccattc ataaacacag cttccaagat gtactccatg tccgaggtca    5400
ggaaacacag ctctgctgac tctgcttgga tcatagtcca tggtcatatc tatgacgcca    5460
cgcgtttctt gaaagatcac cctggtggga ctgacagcat tctcatcaat gctggcactg    5520
attgcactga ggaatttgat gcaattcatt ctgataaggc taagaagctc ttggaggatt    5580
tcaggattgg tgaactcata actactggtt acacctctga ctctcctggc aactccgtgc    5640
acggatcttc ttccttcagc agctttctag cacctattaa ggaacttgtt ccagcgcaga    5700
ggagtgtggc cctaattcca agagagaaaa tcccatgcaa actcatcgac aagcaatcca    5760
tctcccatga tgttaggaaa tttcgatttg cattgccctc tgaggatcaa gtcttgggct    5820
tgcctgttgg aaaacatatc ttcctctgtg ccgttattga cgataagctc tgcatgcgcg    5880
cttacacgcc tactagcacg atcgatgagg tggggtactt cgagttggtt gtcaagatat    5940
acttcaaagg aattcaccct aaattcccca atggagggca aatgtcacag tatcttgatt    6000
ctatgccgtt agggtcattt ctcgacgtga aggtccatt aggtcacatt gaataccaag    6060
gaaagggaaa tttcttagtt catggcaaac agaagtttgc caagaagttg gccatgatag    6120
caggtggaac aggaataact ccagtgtatc aagtcatgca ggcaattctg aaagatccag    6180
aagatgacac agaaatgtat gtggtgtatg ctaacagaac agaggatgat attttactta    6240
aggaagagct tgattcatgg gctgagaaaa ttccagagag ggttaaagtt tggtatgtgg    6300
ttcaggattc tattaaagaa ggatggaagt acagcattgg ttttattaca gaagccattt    6360
```

-continued

```
tgagagaaca tatccctgag ccatctcaca caacactggc tttggcttgt ggaccacctc    6420
ctatgattca atttgctgtt aatccaaact tggagaagat gggctatgac attaaggatt    6480
ccttattggt gttctaattt taaaaacaaa acaatatctg caggaataaa ttttttttt     6540 cccctatca gttgtacata ttgtatttgg tttatcaccc ccatgtacta cgtagtgttt     6600
gtagttctta cattttatt ttttagaatt ttttaaacc ttaggatata aaggttttct      6660
cttccaacaa agtgattctt tagggaagaa atgtactgta ctgtactagt atgtctaagc    6720
cgaaagttgt aatgtttacc atgacaaatt gtattcaatt cctcatggaa tagtaacatt    6780
gtgttcatgt gtcttcctgt aagcgatctt caaaatatca atgtatatat atagtaattg    6840
caaaccattg ttccttttcc cgatgtagtt aactactctt tctttagctt ctagtctctg    6900
gtgaatattt ttttttctat aactctttaa ttaatacggc cttaaataag agaaaagttt    6960
aaaccacgaa tatcattatg cagacgtata ggtaattaat ctactttttg aaaaaaaatc    7020
tattttcttt atgtggtcct tcaaaataat attctagaac cttttgtata ttccctttta    7080
acttctattt agtttt                                                    7096
```

<210> SEQ ID NO 5
<211> LENGTH: 10
<212> TYPE: PRT
<213> ORGANISM: Nicotiana tabacum
<220> FEATURE:
<221> NAME/KEY: MISC_FEATURE
<222> LOCATION: (3)..(3)
<223> OTHER INFORMATION: Lys or Arg
<220> FEATURE:
<221> NAME/KEY: MISC_FEATURE
<222> LOCATION: (4)..(4)
<223> OTHER INFORMATION: Ser or Thr
<220> FEATURE:
<221> NAME/KEY: MISC_FEATURE
<222> LOCATION: (5)..(5)
<223> OTHER INFORMATION: Ile or Val or Ala
<220> FEATURE:
<221> NAME/KEY: MISC_FEATURE
<222> LOCATION: (7)..(7)
<223> OTHER INFORMATION: Thr or Ser

<400> SEQUENCE: 5

Leu Lys Xaa Xaa Xaa Ser Xaa Pro Phe Met
1               5                   10

<210> SEQ ID NO 6
<211> LENGTH: 10
<212> TYPE: PRT
<213> ORGANISM: Nicotiana tabacum
<220> FEATURE:
<221> NAME/KEY: MISC_FEATURE
<222> LOCATION: (3)..(3)
<223> OTHER INFORMATION: Lys or Arg
<220> FEATURE:
<221> NAME/KEY: MISC_FEATURE
<222> LOCATION: (4)..(4)
<223> OTHER INFORMATION: Ser or Thr
<220> FEATURE:
<221> NAME/KEY: MISC_FEATURE
<222> LOCATION: (5)..(5)
<223> OTHER INFORMATION: Ile or Val or Ala
<220> FEATURE:
<221> NAME/KEY: MISC_FEATURE
<222> LOCATION: (7)..(7)
<223> OTHER INFORMATION: Thr or Ser

<400> SEQUENCE: 6

Leu Lys Xaa Xaa Xaa Ser Xaa Pro Phe Ile
1               5                   10

```
<210> SEQ ID NO 7
<211> LENGTH: 10
<212> TYPE: PRT
<213> ORGANISM: Nicotiana tabacum

<400> SEQUENCE: 7

Leu Lys Lys Ser Ile Ser Thr Pro Phe Met
1               5                   10

<210> SEQ ID NO 8
<211> LENGTH: 10
<212> TYPE: PRT
<213> ORGANISM: Nicotiana tabacum

<400> SEQUENCE: 8

Leu Lys Lys Ser Ile Ser Thr Pro Phe Ile
1               5                   10

<210> SEQ ID NO 9
<211> LENGTH: 10
<212> TYPE: DNA
<213> ORGANISM: Nicotiana tabacum

<400> SEQUENCE: 9
ctccattcat                                                            10

<210> SEQ ID NO 10
<211> LENGTH: 10
<212> TYPE: DNA
<213> ORGANISM: Nicotiana tabacum

<400> SEQUENCE: 10
aacacagctt                                                            10

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11 ccactttttta cggacggtta tct                                            23

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
gcaaatcgaa atttcctaac atcat                                           25

<210> SEQ ID NO 13
<211> LENGTH: 6
<212> TYPE: PRT
<213> ORGANISM: Nicotiana tabacum

<400> SEQUENCE: 13

Lys Ser Ile Ser Thr Pro
1               5
```

1

MODULATION OF NITRATE LEVELS IN PLANTS VIA MUTATION OF NITRATE REDUCTASE

FIELD OF THE INVENTION

The present invention relates to plants having reduced nitrate levels, plant cells derived from the plants, products generated from the plants, and methods of modulating nitrate levels in plants by mutating a nitrate reductase enzyme.

BACKGROUND

Certain plants—such as tobacco plants—accumulate high levels of free nitrate in their leaves, which is undesirable because high levels of nitrate have been associated with the formation of carcinogenic compounds referred to as tobacco-specific nitrosamines (TSNAs). TSNAs are a class of compounds that are predominantly produced during the curing of tobacco leaves, though additional formation can occur in the subsequent processing and storage of leaf, and possibly via pyrosynthesis during combustion. Two of the TSNAs found in the cured leaf, N-nitrosonornicotine (NNN) and 4-(methylnitrosamino)-I-(3-pyridyl)-I-butanone (NNK), are classified as Group I carcinogens (the highest designation) by the International Agency for Research on Cancer. Due to the volume of evidence implicating these compounds with various tobacco-associated cancers, the World Health organization has recommended that mandates be implemented to ensure that future tobacco products have reduced levels of these toxicants. TSNAs represent nitrosation products of tobacco alkaloids. In air-cured tobaccos there is a general consensus that nitrite is the agent directly responsible for TSNA formation. Due to its cellular toxicity, however, endogenous nitrite levels are typically very low in plant tissues. Instead, it is believed that the great majority of the nitrite involved in TSNA formation is derived from the nitrate reductase activity of microbes residing on the leaf surface during the 6-10 week curing process that converts a portion of the leaf nitrate pools to nitrite as cellular membranes and organelles become degraded during this period.

TSNAs are formed primarily during the curing process of leaves and involve the nitrosation of tobacco alkaloids. Genetic strategies to lower TSNA content and levels in the cured leaf have focused on targeting either: (1) the alkaloid precursor(s); or (2) the nitrosating agent(s) involved. Most efforts to reduce TSNAs at the level of altering the genetics of tobacco have targeted the alkaloid precursors to TSNAs. Such strategies provide substantial reductions in NNN through the downregulation of the gene family responsible for the synthesis of its alkaloid precursor nomicotine.

Modified tobacco plants having reduced nitrate levels are described by the present applicant in WO2016/046288. As described therein, the expression or activity of a nitrate reductase enzyme is deregulated. The deregulated nitrate reductase enzyme has an amino acid substitution at a position corresponding to position 523 of the polypeptide encoding nitrate reductase. The mutation is referred to as S523D. Overexpression of the mutant nitrate reductase enzyme gave a dramatic increase in nitrate assimilation, resulting in low nitrate/TSNA content and higher amino acid levels. Plants displayed 90% less nitrate compared to the control.

It can be desirable to develop non-genetically modified organism (non-GMO) approaches to reduce nitrate accumulation. Due to the difficulties of growing and commercialising genetically modified crops in countries, including Europe, it can be advantageous to work with mutants featuring single nucleotide polymorphisms rather than mutants obtained through the use of genetic engineering techniques.

Accordingly, there remains a continuing need in the art for reducing nitrate levels in plants, especially via non-transgenic approaches.

SUMMARY OF THE INVENTION

The present invention is based, at least in part, on the finding that mutating *Nicotiana tabacum* nitrate reductase (NIA2) via a non-transgenic approach can result in plants or plant material in which the cured leaves thereof contain modulated (for example, reduced) levels of nitrate as compared to cured leaves derived from a control plant. One such mutation that is described herein is located in the nitrate reductase kinase recognition site within the hinge 1 domain of *Nicotiana tabacum* nitrate reductase.

Hardin et al. (2009) *Biochem. J.* 422:305-312 teaches that oxidation of methionine at position 538 in the NIA2 protein of *Arabidopsis thaliana* is a mechanism to inhibit phosphorylation of NIA protein. Oxidation prevents 14-3-3 binding to nitrate reductase and prevents inactivation of nitrate reductase when exposed to reactive oxygen species (ROS), such as hydrogen peroxide, hydroxyl radicals. Since nitrate reductase converts nitrate to nitrite, leading to production of ammonia and amino acids, a higher activation of nitrate reductase is expected to lower the nitrate level as demonstrated in WO2016/046288. Therefore, oxidation of M538 in the NIA2 protein of *Arabidopsis thaliana* to methionine sulfoxide is expected to lead to lower nitrate levels. M527 in the *Nicotiana tabacum* NIA2 protein corresponds to M538 in *Arabidopsis thaliana* NIA2. The properties of the mutant *Nicotiana tabacum* plants described herein are unexpected. The *Nicotiana tabacum* NIA2 mutant M527I (as it is well understood in the art, M527I means that methionine (M) at position 527 is substituted for isoleucine (I)) comprises the substitution of methionine at position 537 with an isoleucine, which cannot be oxidized. Methionine is known to be oxidized on the sulphur residue to methionine sulfoxide, while isoleucine does not possess any sulphur residue in their structure. Based on this difference, *Nicotiana tabacum* NIA2 mutant M527I would not be expected to stimulate nitrate reductase activation upon exposure to ROS, and as a result, a mechanism for reducing nitrate levels in the plant is eliminated. However, it has been surprisingly found that, despite the substitution of the methionine, the mutant plant of the present disclosure exhibits a reduction in nitrate levels.

Producing plants according to the present disclosure provides a number of other advantages. For example, the plants described herein can be non-genetically modified plants which overcomes the difficulties of growing and commercialising genetically modified crops. By way of further example, reduction in nitrate levels can be achieved without impacting plant total harvest biomass, and nicotine, total alkaloid, ammonia or reducing sugar content in leaves. This can improve the commercial acceptance of the plants, plant material, or plant products.

In one aspect, there is disclosed a plant cell comprising: (a) a polynucleotide sequence encoding a nitrate reductase polypeptide comprising a contiguous polypeptide sequence of SEQ ID NO: 5 or SEQ ID NO: 7, wherein methionine is substituted for an amino acid that reduces nitrate reductase activity in the plant cell as compared to a control plant cell; (b) a polypeptide sequence encoded by the polynucleotide sequence set forth in (a); or (c) a construct, vector or expression vector comprising the polynucleotide sequence set forth in (b).

Suitably, methionine is substituted for a different amino acid, more suitably, the substituted amino acid is isoleucine, more suitably wherein the polypeptide comprises the contiguous polypeptide sequence of SEQ ID NO: 6 or SEQ ID NO: 8

Suitably, the nitrate reductase polypeptide comprises an amino acid substitution at a position corresponding to position 527 of a sequence having at least 80% sequence identity to SEQ ID NO: 1.

Suitably, the nitrate reductase polypeptide comprises, consists or consists essentially of the polypeptide sequence set forth in SEQ ID NO: 3.

Suitably, the polynucleotide sequence comprises, consists or consists essentially a polynucleotide sequence having at least 80% sequence identity to SEQ ID NO: 4.

Suitably, the polynucleotide sequence comprises, consists or consists essentially of the polynucleotide sequence set forth in SEQ ID NO: 4.

Suitably, the plant cell is a *Nicotiana tabacum* plant cell.

Suitably, the plant cell is a plant cell from a *Nicotiana tabacum* AA37 cultivar.

In another aspect, there is disclosed a plant or part thereof comprising the plant cell according to any preceding claim; suitably, wherein cured leaves of the plant or part thereof contain lower levels of nitrate as compared to a control plant or part thereof, suitably, wherein the level of nitrate is reduced by about 37% or more as compared to the control plant or part thereof.

In another aspect, there is disclosed plant material, cured plant material, or homogenized plant material, derived from the plant or part thereof described herein, suitably, wherein the cured plant material is air-cured or sun-cured or flue-cured plant material; suitably, wherein the plant material, cured plant material, or homogenized plant material comprises biomass, seed, stem, flowers, or leaves from the plant or part thereof.

In another aspect, there is disclosed a tobacco product comprising the plant cell described herein, a part of the plant described herein or the plant material described herein.

In another aspect, there is disclosed a method for producing the plant described herein, comprising the steps of: (a) providing the plant cell described herein; and (b) propagating the plant cell into a plant.

In another aspect, there is disclosed a method for producing cured plant material with an altered amount of nitrate as compared to control plant material, comprising the steps of: (a) providing a plant or part thereof as described herein or the plant material as described herein; (b) optionally harvesting the plant material from the plant or part thereof; and (c) curing the plant material.

Suitably, the plant material comprises cured leaves.

Suitably, the curing method is selected from the group consisting of air curing, fire curing, smoke curing, and flue curing.

DEFINITIONS

Figure 1:
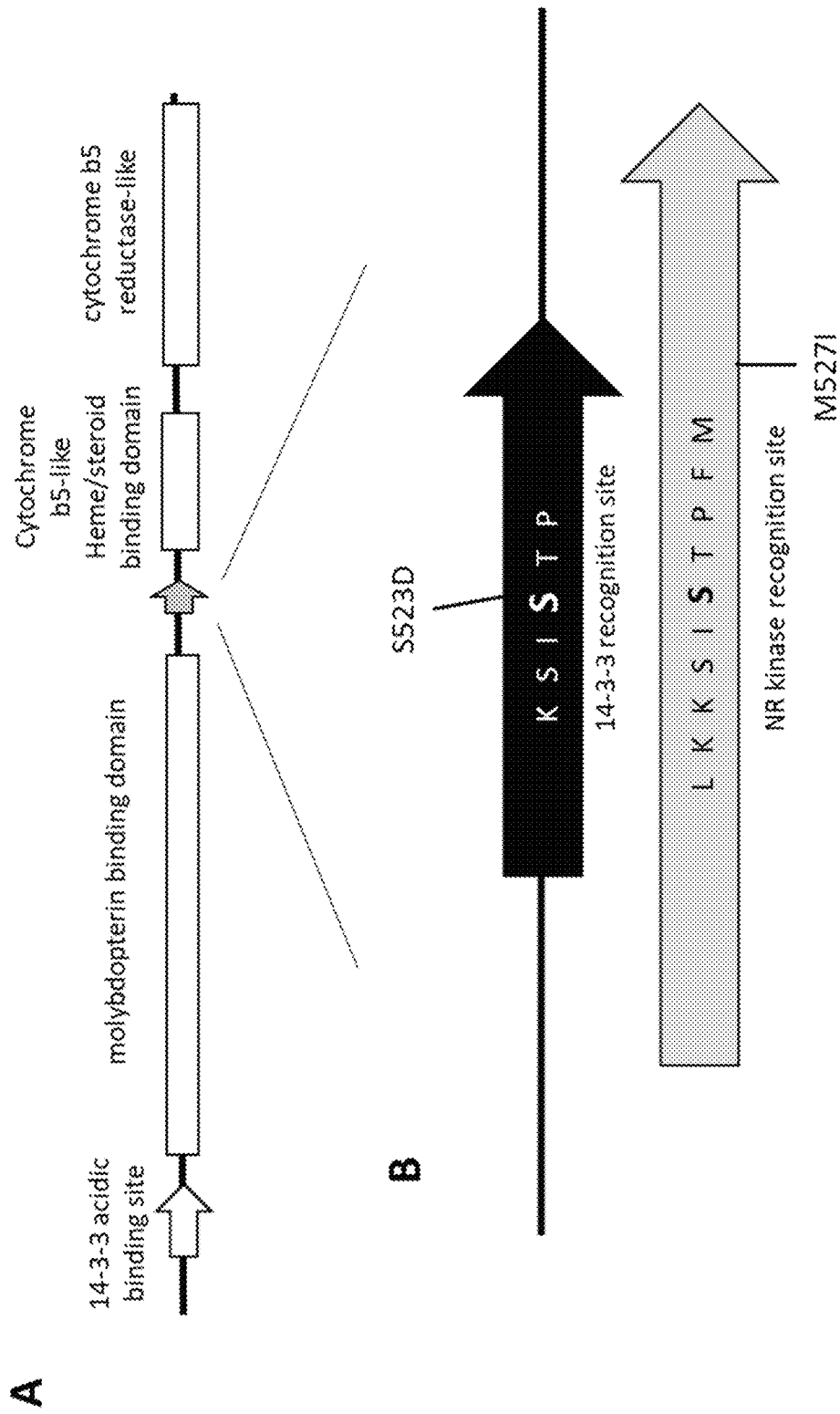
FIG. 1 illustrates the domains and consensus sequences of the NtNIA2 protein sequence. (A) Major domains of *Nicotiana tabacum* nitrate reductase NIA2 protein (GenBank: X14059). (B) Nitrate reductase kinase recognition site (LKKSISTPFW SEQ NO: 7) and 14-3-3 recognition site (KSISTP. SEQ ID NO: 13) within the hinge 1 of NtNIA2. Indicated are the positions of the S523D mutation from WO2016/046288 and the M5271 mutation described herein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures.

The singular forms "a," "and" and "the" include plural references unless the context clearly dictates otherwise.

The term "and/or" means (a) or (b) or both (a) and (b).

The present disclosure contemplates other embodiments "comprising," "consisting of" and "consisting essentially of" the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used throughout the specification and the claims, the following terms have the following meanings:

"Coding sequence" or "polynucleotide encoding" means the nucleotides (RNA or DNA molecule) that comprise a polynucleotide which encodes a polypeptide. The coding sequence can further include initiation and termination signals operably linked to regulatory elements including a promoter and polyadenylation signal capable of directing expression in the cells of an individual or mammal to which the polynucleotide is administered. The coding sequence may be codon optimized.

"Complement" or "complementary" can mean Watson-Crick (for example, A-T/U and C-G) or Hoogsteen base pairing between nucleotides or nucleotide analogs. "Complementarity" refers to a property shared between two polynucleotides, such that when they are aligned antiparallel to each other, the nucleotide bases at each position will be complementary.

"Construct" refers to a double-stranded, recombinant polynucleotide fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" in the context of a control plant or a control plant cell means a plant or plant cell in which the expression, function or activity of one or more genes or polypeptides has not been modified (for example, increased or decreased) and so it can provide a comparison with a plant in which the expression, function or activity of the same one or more genes or polypeptides has been modified. As used herein, a "control plant" is a plant that is substantially equivalent to a test plant or modified plant in all parameters with the exception of the test parameters. For example, when referring to a plant into which a mutation has been introduced, a control plant is an equivalent plant into which the mutation has not been introduced. The control plant can be an outsegregant control plant.

"Expression" refers to the production of a functional product. For example, expression of a polynucleotide fragment may refer to transcription of the polynucleotide fragment (for example, transcription resulting in mRNA or functional RNA) and/or translation of mRNA into a precursor or mature polypeptide.

"Functional" and "full-functional" describes a polypeptide that has biological function or activity. A "functional gene" refers to a gene transcribed to mRNA, which is translated to a functional or active polypeptide.

"Genetic construct" refers to DNA or RNA molecules that comprise a polynucleotide that encodes a polypeptide. The coding sequence can include initiation and termination signals operably linked to regulatory elements including a promoter and polyadenylation signal capable of directing expression.

The terms "homology" or "similarity" refer to the degree of sequence similarity between two polypeptides or between two polynucleotide molecules compared by sequence alignment. The degree of homology between two discrete polynucleotides being compared is a function of the number of identical, or matching, nucleotides at comparable positions.

"Identical" or "identity" in the context of two or more polynucleotides or polypeptides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. The popular multiple alignment program ClustalW (Nucleic Acids Research (1994) 22, 4673-4680; Nucleic Acids Research (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. In particular, an isolated polynucleotide is separated from open reading frames that flank the desired gene and encode polypeptides other than the desired polypeptide. The term "purified" as used herein denotes that a polynucleotide or polypeptide gives rise to essentially one band in an electrophoretic gel. Particularly, it means that the polynucleotide or polypeptide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Modulate" or "modulating" refers to causing or facilitating a qualitative or quantitative change, alteration, or modification in a process, pathway, function or activity of interest. Without limitation, such a change, alteration, or modification may be an increase or decrease in the relative process, pathway, function or activity of interest. For example, gene expression or polypeptide expression or polypeptide function or activity can be modulated. Typically, the relative change, alteration, or modification will be determined by comparison to a control.

The term 'non-naturally occurring' describes an entity—such as a polynucleotide, a genetic mutation, a polypeptide, a plant, a plant cell and plant material—that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. By way of example, a non-naturally occurring entity can be an entity that has been mutated by methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods. For example, chemical mutagenesis can be used which involves the use of exogenously added chemicals—such as mutagenic, teratogenic, or carcinogenic organic compounds—to induce mutations. Mutants with advantageous properties can then be selected and identified. "Oligonucleotide" or "polynucleotide" means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). Hybridization stringency increases as the propensity to form DNA duplexes decreases. In polynucleotide hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments. DNA duplexes are stabilised by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions. To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium. "Stringent hybridization conditions" are conditions that enable a probe, primer, or oligonucleotide to hybridize only to its specific sequence. Stringent conditions are sequence-dependent and will differ. Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Suitably, the conditions are such that sequences at least about 65%, 70%, 75%, 85%, 90%, 95%, 98%, or 99% homologous to each other typically remain hybridized to each other.

"Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 μg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)).

"Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein.

"Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, the polynucleotides include their corresponding RNA sequences, and their complementary (for example, completely complementary) DNA or RNA sequences, including the reverse complements thereof. The polynucleotides of the present disclosure are set forth in the accompanying sequence listing.

"Polypeptide" or "polypeptide sequence" refer to a polymer of amino acids in which one or more amino acid residues is an artificial chemical analogue of a corresponding naturally occurring amino acid, as well as to naturally occurring polymers of amino acids. The terms are also inclusive of modifications including, but not limited to, glycosylation, lipid attachment, sulfation, gamma-carboxylation of glutamic acid residues, hydroxylation and ADP-ribosylation. The polypeptides of the present disclosure are set forth in the accompanying sequence listing.

"Recombinant" as used herein refers to an artificial combination of two otherwise separated segments of sequence—such as by chemical synthesis or by the manipulation of isolated segments of polynucleotides by genetic engineering techniques. The term also includes reference to a cell or vector, that has been modified by the introduction of a heterologous polynucleotide or a cell derived from a cell so modified, but does not encompass the alteration of the cell or vector by naturally occurring events (for example, spontaneous mutation, natural transformation or transduction or transposition) such as those occurring without deliberate human intervention.

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared and/or obtained, as described herein. It is understood that "tobacco" refers to *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured, and/or fermented according to conventional techniques in tobacco preparation.

"Variant" with respect to a peptide or polypeptide means a peptide or polypeptide that differs in sequence by the insertion, deletion, or conservative substitution of amino acids, but retain at least one biological function or activity. Variant may also mean a polypeptide that retains at least one biological function or activity. A conservative substitution of an amino acid, that is, replacing an amino acid with a different amino acid of similar properties (for example, hydrophilicity, degree and distribution of charged regions) is recognized in the art as typically involving a minor change.

The term "variety" refers to a population of plants that share constant characteristics which separate them from other plants of the same species. While possessing one or more distinctive traits, a variety is further characterized by a very small overall variation between individuals within that variety. A variety is often sold commercially.

"Vector" refers to a polynucleotide vehicle that comprises a combination of polynucleotide components for enabling the transport of polynucleotides, polynucleotide constructs and polynucleotide conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleotide plasmids; linearized double-stranded nucleotide plasmids; and other vectors of any origin.

An "expression vector" as used herein is a polynucleotide vehicle that comprises a combination of polynucleotide components for enabling the expression of polynucleotide(s), polynucleotide constructs and polynucleotide conjugates and the like. Suitable expression vectors include episomes capable of extra-chromosomal replication such as circular, double-stranded nucleotide plasmids; linearized double-stranded nucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and polypeptide and polynucleotide chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

"Genome editing" refers to changing an endogenous gene that encodes an endogenous polypeptide, such that polypeptide expression of a truncated endogenous polypeptide or an endogenous polypeptide having an amino acid modification—such as a substitution—is obtained. Genome editing can include replacing the region of the endogenous gene to be targeted or replacing the entire endogenous gene with a copy of the gene that has a truncation or an amino acid substitution with a repair mechanism—such as homology-directed repair. Genome editing may also include generating an amino acid substitution in the endogenous gene by generating a double stranded break in the endogenous gene that is then repaired using NHEJ. NHEJ may add or delete at least one base pair during repair which may generate an amino acid substitution. Genome editing may also include deleting a gene segment by the simultaneous action of two nucleases on the same DNA strand in order to create a truncation between the two nuclease target sites and repairing the DNA break by NHEJ.

"Homology-directed repair" or "HDR" refers to a mechanism in cells to repair double strand DNA lesions when a homologous piece of DNA is present in the nucleus, mostly in G2 and S phase of the cell cycle. HDR uses a donor DNA or donor template to guide repair and may be used to create specific sequence changes to the genome, including the targeted addition of whole genes. If a donor template is provided along with the site specific nuclease, then the cellular machinery will repair the break by homologous recombination, which is enhanced several orders of magnitude in the presence of DNA cleavage. When the homologous DNA piece is absent, NHEJ may take place instead.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Site-specific nuclease" refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), CRISPR/Cas9-based systems, and meganucleases.

"Transcription activator-like effector" or "TALE" refers to a polypeptide structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence. A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion polypeptides of the catalytic domain of a nuclease, such as endonuclease FokI, and a designed TALE DNA-binding domain that may be targeted to a custom DNA sequence.

A "TALEN monomer" refers to an engineered fusion polypeptide with a catalytic nuclease domain and a designed TALE DNA-binding domain. Two TALEN monomers may be designed to target and cleave a TALEN target region.

"Zinc finger" refers to a polypeptide structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" refers to a chimeric polypeptide molecule comprising at least one zinc finger DNA binding domain effectively linked to at least one nuclease or part of a nuclease capable of cleaving DNA when fully assembled.

DETAILED DESCRIPTION

In one aspect, there is provided an isolated polynucleotide sequence encoding a nitrate reductase polypeptide comprising a contiguous polypeptide sequence of SEQ ID NO: 5, wherein methionine is substituted for an amino acid that reduces nitrate reductase activity as compared to a control plant cell.

Suitably, the nitrate reductase polypeptide has a contiguous polypeptide sequence of SEQ ID NO: 7, wherein methionine is substituted for an amino acid that reduces nitrate reductase activity as compared to a control plant cell.

Suitably, the isolated polynucleotide sequence encodes a nitrate reductase polypeptide in which methionine is substituted for a different amino acid, preferably for an aliphatic non-polar amino acid, more preferably an isoleucine.

Suitably, the aliphatic non-polar amino acid is selected from the group of amino acids consisting of glycine, alanine, proline, isoleucine, leucine or valine.

Suitably, the aliphatic non-polar amino acid is isoleucine. According to this embodiment, the nitrate reductase has a substituted contiguous polypeptide sequence of SEQ ID NO: 6 or SEQ ID NO: 8.

Suitably, the isolated polynucleotide sequence encodes a nitrate reductase polypeptide comprising, consisting or consisting essentially of an amino acid substitution at a position corresponding to position 527 of a sequence having at least 80% sequence identity to SEQ ID NO: 1.

Suitably, the isolated polynucleotide sequence encodes a nitrate reductase polypeptide comprising, consisting or consisting essentially of the sequence set forth in SEQ ID NO: 3.

Suitably, the isolated polynucleotide sequence comprises, consists or consists essentially of a sequence having at least 80% sequence identity to SEQ ID NO: 2.

Suitably, the polynucleotide sequence comprises, consists or consists essentially of the polynucleotide sequence set forth in SEQ ID NO: 4.

An exemplary substitution mutation according to the present disclosure is set forth in Table 1.

In certain embodiments, the polynucleotide sequence comprises, consists or consists essentially of a sequence having at least 80% sequence identity to any of the sequences described herein, including any of the polynucleotides shown in the sequence listing.

Suitably, the isolated polynucleotide comprises, consists or consists essentially of a sequence having at least 80%, 85%, 87%, 88%, 89%, 90%, 91%, 92%, 93%, 94%, 95% 96%, 97%, 98%, 99% or 100% sequence identity thereto.

Suitably, the polynucleotide(s) described herein encode an active nitrate reductase polypeptide that has at least about 30%, 40%, 50%, 60%, 70%, 80% or 90% of the function or activity of the polypeptide(s) shown in the sequence listing.

In another embodiment, there is provided polynucleotide fragments of SEQ ID NO. 4 encoding a polypeptide sequence including the M527I mutation with substantial homology (that is, sequence similarity) or substantial identity thereto that have at least about 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO. 4.

Fragments of the polynucleotides incorporating the mutation(s) described herein are also disclosed. Polynucleotide fragments typically comprise at least 10, at least 20, at least 30, at least 40, at least 50, at least 100 or at least 200 contiguous nucleotides.

A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) or truncate(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, they include their corresponding RNA sequences, and their complementary (for example, completely complementary) DNA or RNA sequences, including the reverse complements thereof.

A polynucleotide as described herein will generally contain phosphodiester bonds. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

Analogue polynucleotides can include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in hybridisation assays or primers for use in amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide comprising the use of the probes or primers or both. Exemplary primers are described herein.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the polypeptide sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries include cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under decreased stringency conditions, typically moderately stringent conditions, and commonly highly stringent conditions to the polynucleotide(s), as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y. and can be readily determined by those having ordinary skill in the art based on, for example, the length or base composition of the polynucleotide.

One way of achieving moderately and high stringent conditions are defined herein. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a first sequence is positioned in the 5'-to-3' direction, and if a second sequence is positioned in the 5'-to-3' direction within the same polynucleotide molecule/strand, then the first sequence and the second sequence are orientated in the same direction, or have the same orientation. Typically, a promoter sequence and a gene of interest under the regulation of the given promoter are positioned in the same orientation. However, with respect to the first sequence positioned in the 5'-to-3' direction, if a second sequence is positioned in the 3'-to-5' direction within the same polynucleotide molecule/strand, then the first sequence and the second sequence are orientated in anti-sense direction, or have anti-sense orientation. Two sequences having anti-sense orientations with respect to each other can be alternatively described as having the same orientation, if the first sequence (5'-to-3' direction) and the reverse complementary sequence of the first sequence (first sequence positioned in the 5'-to-3') are positioned within the same polynucleotide molecule/strand. The sequences set forth herein are shown in the 5'-to-3' direction.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

In one aspect, there is provided an isolated polypeptide comprising, consisting or consisting essentially of a polypeptide having at least 80% sequence identity to any of the polypeptides described herein, including any of the polypeptides shown in the sequence listing. Suitably, the isolated polypeptide comprises, consists or consists essentially of a sequence having at least 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In another aspect, there is disclosed a polypeptide sequence encoded by the polynucleotide sequence described herein.

In another aspect, there is disclosed a nitrate reductase polypeptide comprising a contiguous polypeptide sequence of SEQ ID NO: 5, wherein methionine is substituted for an amino acid that reduces nitrate reductase activity as compared to a control plant cell. The sequence SEQ ID NO: 5 acts as the recognition site for binding of nitrate reductase kinase responsible for the phosphorylation of the NtNIA2 amino acid S523.

Suitably, the nitrate reductase comprises a contiguous polypeptide sequence of SEQ ID NO: 7, wherein methionine is substituted for an amino acid that reduces nitrate reductase activity as compared to a control plant cell.

Suitably, methionine is substituted for a different amino acid—such as an aliphatic non-polar amino acid which can be selected from the group of amino acids consisting of glycine, alanine, proline, isoleucine, leucine or valine.

Suitably, the aliphatic non-polar amino acid is I. According to this embodiment, the nitrate reductase comprises a contiguous polypeptide sequence of SEQ ID NO: 6 or SEQ ID NO: 8.

Suitably, the nitrate reductase polypeptide comprises, consists or consists essentially of an amino acid substitution at a position corresponding to position 527 of a sequence having at least 80% sequence identity to SEQ ID NO: 1.

Suitably, the nitrate reductase polypeptide comprises, consists or consists essentially of the amino acid substitution M527I in a sequence having at least 80% sequence identity to SEQ ID NO: 1.

Suitably, the nitrate reductase polypeptide comprises, consists or consists essentially of the sequence set forth in SEQ ID NO: 3.

Fragments of the polypeptides incorporating the mutation(s) described herein are also disclosed. The fragments of the polypeptide(s) typically retain some or all of the function or activity of the full length sequence. Polypeptide fragments typically comprise at least 10, at least 20, at least 30, at least 40, at least 50, at least 100 or at least 200 contiguous amino acids. The polypeptides disclosed herein include at least one mutation produced by introducing any type of one or more alterations, which can be isolated naturally. Suitably, the function or activity of the nitrate reductase polypeptide into which the mutation(s) is introduced is modulated (for example, reduced) by the introduction of the mutation. Suitably, the mutation is a substitution. A substitution refers to the replacement of at least one amino acid of the nitrate reductase polypeptide with another amino acid having similar properties (such as similar hydrophobicity, hydrophilicity, antigenicity, propensity to form or break alpha-helical structures or β-sheet structures and the like).

Suitably the mutation is a substitution of methionine in the contiguous polypeptide sequence of SEQ ID NO: 5 or SEQ ID NO: 7 in which methionine is substituted for an amino acid in which the plant carrying the substitution has reduced nitrate reductase activity as compared to a control plant. In one embodiment, methionine is substituted for an aliphatic non-polar amino acid—such as glycine, alanine, proline, isoleucine, leucine or valine. In one embodiment the aliphatic non-polar amino acid is isoleucine, suitably the contiguous polypeptide sequence is then SEQ ID NO: 6 or SEQ ID NO: 8. In one embodiment, the substitution is M527I. An exemplary nitrate reductase polypeptide sequence carrying the M527I mutation is SEQ ID NO: 3.

A plant or plant cell comprising or carrying a mutation in one or more polynucleotides or polypeptides described herein is disclosed, wherein said mutation results in modulated function or activity of nitrate reductase. Mutations described herein can include man-made mutations or synthetic mutations. Mutations in the polynucleotides and polypeptides described herein can be mutations that are obtained or obtainable via a process which includes an in vitro or an in vivo manipulation step. Mutations in the polynucleotides and polypeptides described herein can be mutations that are obtained or obtainable via a process which includes intervention by man. There is provided a method for modulating the level of a polypeptide in a (cured) plant or in (cured) plant material said method comprising introducing into the genome of said plant one or more mutations that modulate expression of at least one gene, wherein said at least one mutation is selected from the sequences according to the present disclosure—such as M527I. Suitably, the gene encodes the *Nicotiana tabacum* nitrate reductase polypeptide as described herein.

There is also disclosed a plant or plant cell that is heterozygous or homozygous for one or more mutations according to the present disclosure, wherein said mutation results in modulated expression of the gene or function or activity of the polypeptide encoded thereby. The function or activity of one or more polypeptides of the present disclosure in a plant is increased or decreased if the function or activity is lower or higher than the function or activity of the same polypeptide(s) in a plant that has not been modified to inhibit the function or activity of that polypeptide and which has been cultured, harvested and cured using the same protocols.

Methods for obtaining mutant polynucleotides and polypeptides as described herein are also disclosed. A plant of interest—such as tobacco, including a plant cell or plant material, can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other methods as discussed below.

Methods that introduce mutations randomly in a polynucleotide can include chemical mutagenesis and radiation mutagenesis. Chemical mutagenesis involves the use of exogenously added chemicals—such as mutagenic, teratogenic, or carcinogenic organic compounds—to induce mutations. Mutagens that create primarily point mutations and short deletions, insertions, missense mutations, simple sequence repeats, transversions, and/or transitions, including chemical mutagens or radiation, may be used to create the mutations. Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Methods that introduce one or more targeted mutations into a polynucleotide sequence include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Zinc finger polypeptides can be used to introduce one or more targeted mutations into a polynucleotide sequence. In various embodiments, a genomic DNA sequence comprising a part of or all of the coding sequence of the polynucleotide is modified by zinc finger nuclease-mediated mutagenesis. The genomic DNA sequence is searched for a unique site for zinc finger polypeptide binding. Alternatively, the genomic DNA sequence is searched for two unique sites for zinc finger polypeptide binding wherein both sites are on opposite strands and close together, for example, 1, 2, 3, 4, 5, 6 or more base pairs apart. Accordingly, zinc finger polypeptides that bind to polynucleotides are provided. A zinc finger polypeptide may be engineered to recognize a selected target site in a gene. A zinc finger polypeptide can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the polynucleotide target and that does not occur in the cell or organism comprising the polynucleotide which is to be modified. Methods for the design of zinc finger polypeptide which binds specific polynucleotides which are unique to a target gene are known in the art. Methods for delivering zinc finger polypeptide and zinc finger nuclease to a plant are similar to those described below for delivery of meganuclease.

Meganucleases, such as I-CreI, can be used to introduce one or more targeted mutations into a polynucleotide sequence. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease polypeptides can be delivered into plant cells by a variety of different mechanisms known in the art. Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the function of the engineered meganuclease to cleave and mutate the meganuclease recognition site.

One method of genome editing involves the use of transcription activator-like effector nucleases (TALENs) which induce double-strand breaks which cells can respond to with repair mechanisms. NHEJ reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. For certain applications, it may be desirable to precisely remove the polynucleotide from the genome of the plant. Such applications are possible using a pair of engineered meganucleases, each of which cleaves a meganuclease recognition site on either side of the intended deletion. TALENs that are able to recognize and bind to a gene and introduce a double-strand break into the genome can also be used.

Another method of genome editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) polypeptides to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of polypeptide transcription factors. CRISPR/Cas technology was implemented in plants in the method of international application WO 2015/189693, which discloses a viral-mediated genome editing platform that is broadly applicable across plant species. The RNA2 genome of the tobacco rattle virus (TRV) was engineered to carry and deliver guide RNA into *Nicotiana benthamiana* plants over-expressing Cas9 endonuclease. In the context of the present disclosure, a guide RNA may be derived from any of the sequences disclosed herein and the teaching of WO2015/189693 applied to edit the genome of a plant cell and obtain a desired mutant plant. The fast pace of the development of the technology has generated a great variety of protocols with broad applicability in plantae, which have been well catalogued in a number of recent scientific review articles (for example, *Plant Methods* (2016) 12:8; and *Front Plant Sci.* (2016) 7:506). A review of CRISPR/Cas systems with a particular focus on its application is described in *Biotechnology Advances* (2015) 33, 1, 41-52). More recent developments in the use of CRISPR/Cas for manipulating plant genomes are discussed in *Acta Pharmaceutica Sinica B* (2017) 7, 3, 292-302 and *Curr. Op. in Plant Biol.* (2017) 36, 1-8. CRISPR/Cas9 plasmids for use in plants are listed in "addgene", the non-profit plasmid repository (addgene.org), and CRISPR/Cas plasmids are commercially available.

One or more introduced mutations—such as the mutation described herein—can be identified or selected using methods known to those of skill in the art—such as Southern blot analysis, DNA sequencing, PCR analysis, or phenotypic analysis. Mutations that impact gene expression or that interfere with the function of the encoded polypeptide can be determined using methods that are well known in the art.

The plants or plant cells according to the present disclosure comprise the mutation described and optionally any combination of one or more further mutations in one or more genes. For example, the plants or plant cells may have a single mutation in a single gene; multiple mutations in a single gene; a single mutation in two or more or three or more or four or more genes; or multiple mutations in two or more or three or more or four or more genes. An example of one such mutation is described herein.

In one embodiment, seeds from plants are mutagenised and then grown into first generation mutant plants. The first generation plants are then allowed to self-pollinate and seeds from the first generation plant are grown into second generation plants, which are then screened for mutations—such as the mutation described herein—in their loci. Though the mutagenized plant material can be screened for mutations, an advantage of screening the second generation plants is that all somatic mutations correspond to germline mutations. One of skill in the art will understand that a variety of plant materials, including but not limited to, seeds, pollen, plant tissue or plant cells, may be mutagenised in order to create the mutant plants. However, the type of plant material mutagenised may affect when the plant polynucleotide is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Prepared polynucleotide from individual plants, plant cells, or plant material can optionally be pooled in order to expedite screening for at least the mutation described herein in the population of plants originating from the mutagenized plant tissue, cells or material. One or more subsequent generations of plants, plant cells or plant material can be screened. The size of the optionally pooled group is dependent upon the sensitivity of the screening method used.

After the samples are optionally pooled, they can be subjected to polynucleotide-specific amplification techniques, such as PCR. Any one or more primers or probes specific to the gene or the sequences immediately adjacent to the gene may be utilized to amplify the sequences within the optionally pooled sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

Accordingly, in a further aspect there is provided a method of preparing a plant comprising the mutation described herein. The method involves providing at least one cell of a plant comprising a gene encoding a functional nitrate reductase polynucleotide. Next, the at least one cell of the plant is treated under conditions effective to modulate the function of the nitrate reductase polynucleotide. The at least one mutant plant cell is then propagated into a mutant plant, where the mutant plant has a modulated level of nitrate reductase polypeptide as compared to that of a control plant. In one embodiment, the treating step involves subjecting the at least one cell to a chemical mutagenising agent as described herein and under conditions effective to yield at least one mutant plant cell. In another embodiment of this method, the treating step involves subjecting the at least one cell to a radiation source under conditions effective to yield at least one mutant plant cell. The term "mutant plant" includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. The same technique can also be applied to the introgression of one or more non-naturally occurring mutation(s) from a first plant into a second plant. Plants showing a desired trait may be screened out of a pool of mutant plants. Suitably, the selection is carried out utilising the knowledge of the polynucleotide as described herein. Consequently, it is possible to screen for a genetic trait as compared to a control. Such a screening approach may involve the application of conventional amplification and/or hybridization techniques as discussed herein. Thus, a further aspect of the present disclosure relates to a method for identifying a mutant plant comprising the steps of: (a) providing a sample comprising polynucleotide from a plant; and (b) determining the sequence of the polynucleotide, wherein a difference in the sequence of the polynucleotide as compared to the polynucleotide of a control plant is indicative that said plant is a mutant plant. In another aspect there is provided a method for identifying a mutant plant which accumulates decreased levels of nitrate as compared to a control plant comprising the steps of: (a) providing a sample from a plant to be screened; (b) determining if said sample comprises one or more mutations as described herein in a nitrate reductase polynucleotide; and (c) determining the level of nitrate in said plant. Suitably the level of nitrate is determined in cured leaves. In another aspect there is provided a method for preparing a mutant plant which has decreased levels of nitrate as compared to a control plant comprising the steps of: (a) providing a sample from a first plant; (b) determining if said sample comprises one or more mutations as described herein in a nitrate reductase polynucleotide that results in decreased levels of nitrate; and (c) transferring the one or more mutations into a second plant. Suitably the level of nitrate is determined in cured leaves. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has decreased levels of nitrate as compared to a control plant comprising the steps of: (a) providing a sample from a first plant; (b) determining if said sample comprises one or more mutations as described herein in a nitrate reductase polynucleotide that results in decreased levels of nitrate; and (c) introgressing the one or more mutations from the first plant into a second plant. Suitably the level of nitrate is determined in cured leaves. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the "mutant plants" may have one or more mutations localised only to a specific region of the plant— such as within the sequence of the one or more polynucleotide(s) described herein. According to this embodiment, the remaining genomic sequence of the mutant plant will be the same or substantially the same as the plant prior to the mutagenesis.

In a further aspect there is provided a method of identifying a plant, a plant cell or plant material comprising a mutation in a gene encoding a nitrate reductase polynucleotide comprising: (a) subjecting a plant, a plant cell or plant material to mutagenesis; (b) obtaining a sample from said plant, plant cell or plant material or descendants thereof; and (c) determining the presence of a mutated polynucleotide sequence carrying the mutation described herein.

The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis subsp. hesperis, N. otophora, N. paniculata, N. pauciflora, N. petunioides, N. plumbaginifolia, N. quadrivalvis, N. raimondii, N. repanda, N. rosulata, N. rosulata subsp. ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*.

In one embodiment, the plant is *N. tabacum*.

The use of tobacco cultivars and elite tobacco cultivars is also contemplated herein. The plant may therefore be a tobacco variety or elite tobacco cultivar that comprises one or more genetic mutations. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Nicotiana tabacum varieties include Burley type, dark type, flue-cured type, and Oriental type tobaccos. Non-limiting examples of varieties or cultivars are: AA37, BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter sub-varieties of the above, even if not specifically identified herein, are also contemplated.

In one embodiment, the cultivar is AA37 which is generally understood to be a cross between a South American dark tobacco and American Burley germplasm.

Embodiments are also directed to compositions and methods for producing plants that have been modified to modulate the expression or function of a polynucleotide(s) described herein (or any combination thereof as described herein). Advantageously, the plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a plant described herein. Preferably, the seed is a tobacco seed. A further aspect relates to pollen or an ovule of a plant that is described herein. In addition, there is provided a plant as described herein which further comprises a polynucleotide conferring male sterility.

Also provided is a tissue culture of regenerable cells of the plant as described herein, which culture regenerates plants capable of expressing all the morphological and physiological characteristics of the parent. The regenerable cells include cells from leaves, pollen, embryos, cotyledons, hypocotyls, roots, root tips, anthers, flowers and a part thereof, ovules, shoots, stems, stalks, pith and capsules or callus or protoplasts derived therefrom.

One object is to provide plants or parts thereof that exhibit modulated levels of nitrate in the plant material, for example, in cured leaves. Suitably, the plants or parts thereof exhibit modulated levels of nitrate as compared to a control plant.

Suitably, the plants or parts thereof have substantially the same total harvest biomass (indicated as fresh leaf biomass per plant) as the control plant.

Suitably, the plants or parts thereof have substantially the same level of nicotine leaf content as the control plant.

Suitably, the plants or parts thereof have substantially the same level of total alkaloid leaf content as the control plant.

Suitably, the plants or parts thereof have substantially the same level of ammonia leaf content as the control plant.

Suitably, the plants or parts thereof have substantially the same level of reducing sugar leaf content as the control plant.

Accordingly, there is described herein plants or parts thereof or plant cells that have modulated levels of nitrate as compared to control cells or control plants. The plants or plant cells are modified to modulate the synthesis or function of one or more of the polypeptides described herein by modulating the expression of one or more of the corresponding polynucleotides described herein. Suitably, the modulated levels of nitrate are observed in cured leaves. In certain embodiments, the level of nitrate in the plant—such as the cured leaves or cured tobacco—is reduced.

A further aspect, relates to a plant or plant cell, wherein the expression or the function of one or more of the polypeptides described herein is modulated and a part of the plant (for example, the cured leaves or cured tobacco) have decreased levels of nitrate of at least about 37% therein as compared to a control plant in which the expression or the function of said polypeptide(s) has not been modulated. In certain embodiments, the level of nitrate in the plant—such as the cured leaves or cured tobacco—may be decreased, for example, by at least about 30% or more, or about 35% or more, or about 37% or more, or about 40% or more.

A still further aspect, relates to a cured plant material—such as cured leaf or cured tobacco-derived or derivable from a plant or plant cell as described herein, wherein expression of one or more of the polynucleotides described herein or the function of the polypeptide encoded thereby is modulated and wherein the level of nitrate is modulated by at least about 37% as compared to a control plant, for example, by at least about 30% or more, or about 35% or more, or about 40% or more.

Embodiments are also directed to compositions and methods for producing plants or plant cells that have been modified to modulate the expression or function of the one or more of the polynucleotides or polypeptides described herein which can result in plants or plant components (for example, leaves—such as cured leaves—or tobacco) or plant cells with modulated nitrate content.

An increase in function or activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more.

A reduction in function or activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

A plant carrying the mutation described herein in a nitrate reductase polynucleotide can be used in a plant breeding program to create useful lines, varieties and hybrids. In particular, the mutant can be introgressed into the commercially important varieties described above. Thus, methods for breeding plants are provided, that comprise crossing plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of plants of the disclosure.

In one embodiment, a method is provided for producing a plant comprising: (a) crossing a plant of the present disclosure with a second plant to yield progeny tobacco seed; (b) growing the progeny tobacco seed, under plant growth conditions, to yield a non-naturally occurring plant. The method may further comprise: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the plant of the present disclosure. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. Certain embodiments exclude the step of selecting a plant.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the polynucleotide sequence information for the polynucleotide(s) described herein (or any combination thereof as described herein).

Aside from the mutations described herein, the plants or plant cells described herein can have one or more further mutations either in the same polynucleotides or polypeptides as described herein or in one or more other polynucleotides or polypeptides within the genome. Without limitation, the plants and parts thereof described herein can be modified either before or after the expression, function or activity of the one or more polynucleotides and/or polypeptides according to the present disclosure have been modulated.

One or more of the following further genetic modifications (for example, mutations) can be present in the plants and parts thereof.

One or more genes that are involved in the conversion of nitrogenous metabolic intermediates can be modified (for example, mutated) resulting in lower levels of at least one tobacco-specific nitrosamine (TSNA). Non-limiting examples of such genes include those encoding nicotine demethylase—such as CYP82E4, CYP82E5 and CYP82E10 as described in WO2006/091194, WO2008/070274, WO2009/064771 and WO2011/088180—and nitrate reductase, as described in WO2016046288.

One or more genes that are involved in heavy metal uptake or heavy metal transport can be modified (for example, mutated) resulting in lower heavy metal content. Non-limiting examples include genes in the family of multidrug resistance associated polypeptides, the family of cation diffusion facilitators (CDF), the family of Zrt-Irt-polypeptides (ZIP), the family of cation exchangers (CAX), the family of copper transporters (COPT), the family of heavy-metal ATPases (for example, HMAs, as described in WO2009/074325 and WO2017/129739), the family of homologs of natural resistance-associated macrophage polypeptides (NRAMP), and other members of the family of ATP-binding cassette (ABC) transporters (for example, MRPs), as described in WO2012/028309, which participate in transport of heavy metals—such as cadmium.

Other exemplary modifications (for example, mutations) can result in plants with modulated expression or function of isopropylmalate synthase which results in a change in sucrose ester composition which can be used to alter flavor profile (see WO2013029799).

Other exemplary modifications (for example, mutations) can result in plants with modulated expression or function of threonine synthase in which levels of methional can be modulated (see WO2013029800).

Other exemplary modifications (for example, mutations) can result in plants with modulated expression or function of one or more of neoxanthin synthase, lycopene beta cyclase and 9-cis-epoxycarotenoid dioxygenase to modulate beta-damascenone content to alter flavor profile (see WO2013064499).

Other exemplary modifications (for example, mutations) can result in plants with modulated expression or function of members of the CLC family of chloride channels to modulate nitrate levels therein (see WO2014096283 and WO2015197727).

Other exemplary modifications (for example, mutations) can result in plants with modulated expression or function of one or more asparagine synthetases to modulate levels of asparagine in leaf and modulated levels of acrylamide in aerosol produced upon heating or combusting the leaf (see WO2017042162).

Examples of other modifications (for example, mutations) include modulating herbicide tolerance, for example, glyphosate is an active ingredient of many broad spectrum herbicides.

Another exemplary modification (for example, mutation) results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single polypeptide and significantly delayed the evolution of resistant insects.

Another exemplary modification (for example, mutation) results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered.

Another exemplary modification (for example, mutation) results in altered reproductive capability, such as male sterility.

Another exemplary modification (for example, mutation) results in plants that are tolerant to abiotic stress (for example, drought, temperature, salinity).

Another exemplary modification (for example, mutation) results in plants in which the activity of one or more glycosyltransferases—such as N-acetylglucosaminyltransferase, β(1,2)-xylosyltransferase and a(1,3)-fucosyl-transferase is modulated (see WO/2011/117249).

Another exemplary modification (for example, mutation) results in plants in which the activity of one or more nicotine N-demethylases is modulated such that the levels of nornicotine and metabolites of nornicotine—that are formed during curing can be modulated (see WO2015169927).

Other exemplary modifications (for example, mutations) can result in plants with improved storage polypeptides and oils, plants with enhanced photosynthetic efficiency, plants with prolonged shelf life, plants with enhanced carbohydrate content, and plants resistant to fungi.

One or more genes that are involved in the nicotine synthesis pathway can be modified (for example, mutated) resulting in plants or parts of plants that when cured, produce modulated levels of nicotine. The nicotine synthesis genes can be selected from the group consisting of: A622, BBLa, BBLb, JRE5L1, JRE5L2, MATE1, MATE 2, MPO1, MPO2, MYC2a, MYC2b, NBB1, nic1, nic2, NUP1, NUP2, PMT1, PMT2, PMT3, PMT4 and QPT or a combination of one or more thereof.

One or more genes that are involved in controlling the amount of one or more alkaloids can be modified (for example, mutated) resulting in plants or parts of plants that produce modulated levels of alkaloid. Alkaloid level controlling genes can be selected from the group consisting of; BBLa, BBLb, JRE5L1, JRE5L2, MATE1, MATE 2, MYC2a, MYC2b, nic1, nic2, NUP1 and NUP2 or a combination of two or more thereof.

Parts of the plants described herein, particularly the leaf lamina and midrib of such plants, can be incorporated into or used in making various consumable products including but not limited to aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the plants described herein. Processes of curing green tobacco leaves are known by those having skills in the art and include without limitation air-curing, fire-curing, flue-curing and sun-curing as described herein.

In another embodiment, there is described tobacco products including tobacco-containing aerosol forming materials comprising plant material—such as leaves, preferably cured leaves—from the tobacco plants described herein. The tobacco products described herein can be a blended tobacco product which may further comprise unmodified tobacco.

Products and methods for crop management and agriculture

The plants may have other uses in, for example, agriculture. For example, plants described herein can be used to make animal feed and human food products.

The disclosure also provides methods for producing seeds comprising cultivating the plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one or more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein.

In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in amplification or detection). The one or more specific primers or probes can be designed and used to amplify or detect a part or all of the polynucleotide(s). By way of specific example, two primers may be used in a PCR protocol to amplify a polynucleotide fragment. The PCR may also be performed using one primer that is derived from a polynucleotide sequence and a second primer that hybridises to the sequence upstream or downstream of the polynucleotide sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one or more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one or more primers or probes for specifically detecting at least a portion of the polynucleotide(s). Kits for detecting at least a portion of the polynucleotide(s) are also provided which comprise one or more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for using the kit.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by polynucleotide variability. Thus, the present disclosure further provides a means to follow segregation of one or more genes or polynucleotides as well as chromosomal sequences genetically linked to these genes or polynucleotides using such techniques as AFLP analysis.

The invention is further described in the Examples below, which are provided to describe the invention in further detail. These examples, which set forth a preferred mode presently contemplated for carrying out the invention, are intended to illustrate and not to limit the invention.

EXAMPLE

M0 seeds of *Nicotiana tabacum* AA37 are treated with ethyl-methanesulfonate (EMS) at different concentrations and exposure times, to generate a population of plants with random point mutations. A kill-curve is estimated at M1 generation for each treatment, together with lethality, fertility and rate of chimerism. M1 plants are self-fertilized to generate M2 families of seeds, to allow recessive alleles to be recovered as homozygous and lethal alleles to be recovered as heterozygous. Genomic DNA from eight M2 plants per family of the EMS mutagenised population is extracted and screened for mutants, while M2 plant material and M3 seeds are collected and stored for future analyses. To identify and characterise the mutant variants, genomic DNA samples from M2 plants are pooled in groups and screened by sequencing of targeted gene fragments. Target gene fragments are amplified using the primers specific for tobacco NIA2 gene shown in Table 2. Mutations in the target genes are retrieved by sequencing the individual DNA fragments. The tobacco NIA2 mutation M527I is described in Table 1. A mutant plant is crossed with AA37 wild-type and selfed F1 which is heterozygous. F2 segregants are analysed by a quantitative nucleic acid amplification method (TaqMan).

In a field trial, three NIA2 M527I homozygous mutant lines are tested against 5 outsegregant homozygous wild type lines and 1 AA37 control line which was not subjected to EMS treatment. Field design displayed the plants in 20 plant plots randomly distributed to minimize positional effect due to field inhomogeneity. Plants are grown according to Swiss standard good agricultural practices for burley tobacco. At harvest, total leaf fresh biomass is measured. Leaf plant biomass measurements are taken by cutting leaves at harvest and recording their fresh weights.

Leaves from the second harvest (mid stalk position) are then air cured and samples are analyzed for chemical profiling via standard Skalar methods.

Figure 2:
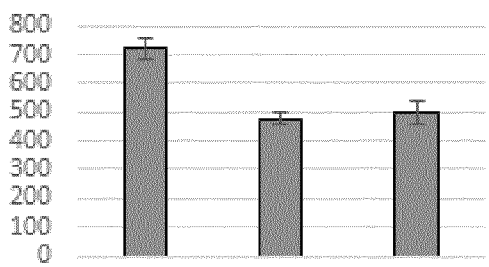
FIG. 2 is a series of bar graphs illustrating the chemical profiling of cured leaves from second harvest and total fresh leaf biomass. (A) Fresh weight (FW) of total harvest leaves expressed as grams per plant; (B) Cured leaves nicotine content expressed as micrograms per gram of cured material; (C) Total alkaloids content expressed as percentage of cured material dry weight; (D) Ammonia content expressed as percentage of cured material dry weight; (E) Reducing sugars content expressed as percentage of cured material dry weight; and (F) Nitrate content expressed as percentage of cured material dry weight. AA37 control indicates lines which were not subjected to EMS treatment (n=6 plots); NIA2_M527I_WT indicated AA37 outsegregant wild type lines (n=15 plots); NIA2_M527I_HOMO indicates NtNIA2 M527I homozygous lines (n=11 plots). Error bars indicate a confidence interval at 95% calculated using t student test.
Figure 2:
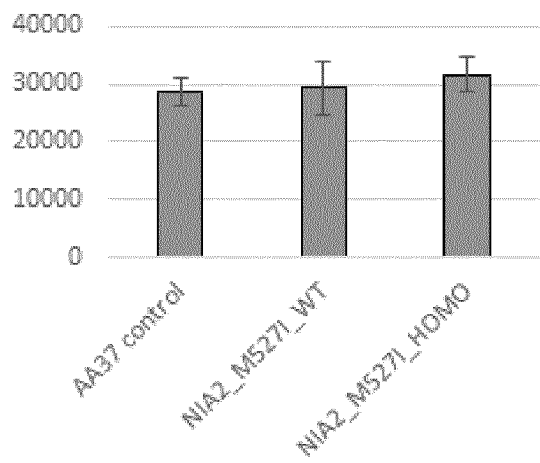
Figure 2:
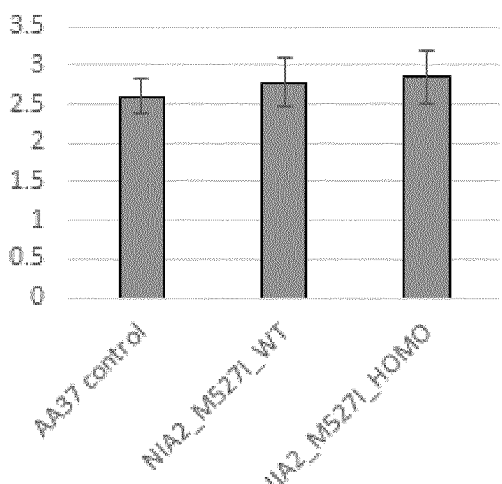
Figure 2:
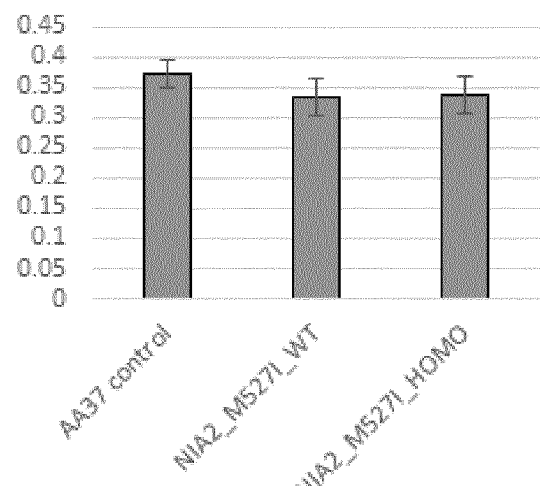
Figure 2:
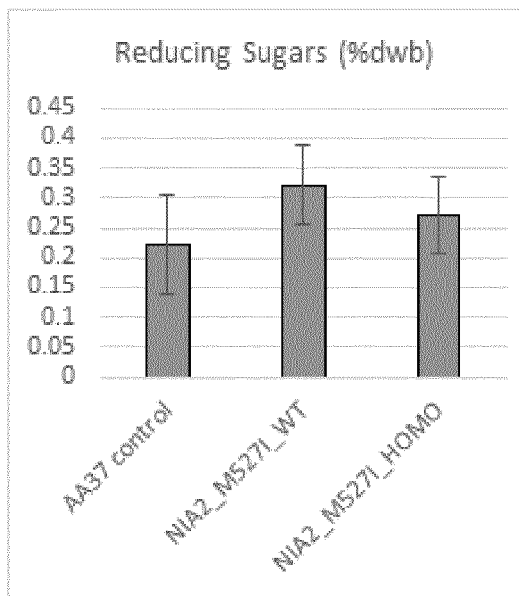
Figure 2:
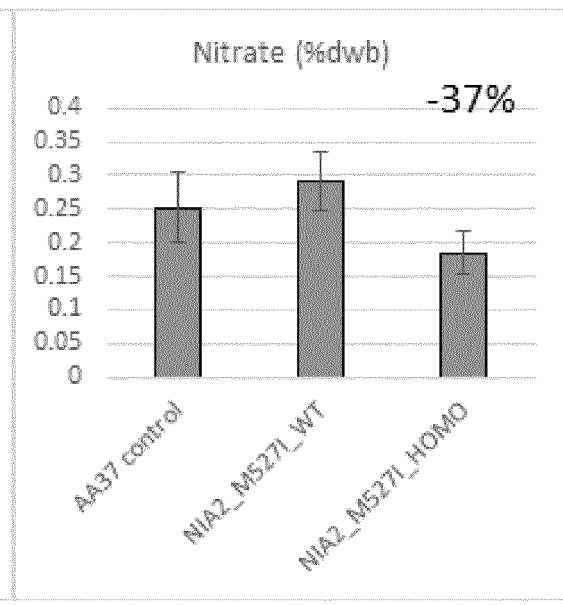

Results are reported in FIG. 2. Mutant plant lines NtNIA2 M527I demonstrate in a field trial a 37% reduction in nitrate levels in cured leaves compared to out-segregant wild type control plants. No effect on plant total harvest biomass (indicated as fresh leaf biomass per plant) and on nicotine, total alkaloids, ammonia and reducing sugars leaf content is observed.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the claims.

SEQUENCE LISTING

SEQ ID NO: 1 Wild type polypeptide sequence of *Nicotiana tabacum* NIA2 gene for nitrate reductase, GenBank Accession number X14059. The sequence which acts as the recognition site for binding of the nitrate reductase kinase responsible for the phosphorylation of NtNIA2 amino acid S523 is highlighted in bold and underline.

MAASVENRQFSHLEAGLSRSFKPRSDSPVRGCNFPSPNSINFQKKPNSTIYLDYSSSEDDDDDDEKNEYL
QMIKKGNSELEPSVHDIRDEGTADNWIERNFSMIRLIGKHPFNSEPPLNRLMHHGFITPVPLHYVRNHGP
VPKGTWDDWTVEVTGLVKRPMKFTMDQLVNEFPCRELPVTLVCAGNRRKEQNMVKQTIGFNWGAAAVSTT
IWRGVPLRALLKRCGVFSKNKGALNVCFEGADVLPGGGGSKYGTSIKKEFAMDPARDIIVAYMQNGEKLA
PDHGFPVRMIIPGFIGGRMVKWIKRIIVITQESDSYYHFKDNRVLPPHVDAELANTEAWWYKPEYIINEL
NINSVITTPCHEEILPINAWITQRPYILRGYSYSGGGKKVIRVEVILDGGETWQVSTLDHPEKPIKYGKY
WCWCFWSLEVEVLDLLSAKEIAVRAWDETLNIQPEKLIWNVMGMMNNCWERVKMNVCKPHKGEIGIVFEH
PIQPGNQSGGWMAKERHLEISAEAPQTLKKSISTPFMNTASKMYSMSEVRKHSSADSAWIIVHGHIYDAT
RFLKDHPGGIDSILINAGTDCTEEFDAIHSDKAKKLLEDFRIGELITTGYISDSPGNSVHGSSSFSSFLA
PIKELVPAQRSVALIPREKIPCKLIDKQSISHDVRKFRFALPSEDQVLGLPVGKHIFLCAVIDDKLCMRA
YIPTSTIDEVGYFELVVKIYFKGIHPKFPNGGQMSQYLDSMPLGSFLDVKGPLGHIEYQGKGNFLVHGKQ
KFAKKLAMIAGGIGITPVYQVMQAILKDPEDDTEMYVVYANRTEDDILLKEELDSWAEKIPERVKVWYVV
QDSIKEGWKYSIGFITEAILREHIPEPSHTTLALACGPPPMIQFAVNPNLEKMGYDIKDSLLVF

SEQ ID NO: 2 Wild type polynucleotide sequence of *Nicotiana tabacum* NIA2 gene for nitrate reductase, GenBank Accession number X14059. The sequence which acts as the recognition site for binding of the nitrate reductase kinase responsible for the phosphorylation of NtNIA2 amino acid S523 is highlighted in bold and underline.

```
   1 tacatacaag ggcgcgaata aacttttttt aaagtaaatg tatatgaact tgcaatgaaa
  61 gaggaccttA acttgtttgt ctttgttgct ttctgcaaat ttcaccttaa cagcccattt
 121 gagattgatt tagttagtta taacaattag ttaaatgctt gtgtaatttg aagaaaatat
 181 ttggacgtgc tcgctgaaaa cattatactc ctatataata gaaatacttt ctgaaaagtt
 241 ggtcttgttc aaaaacgtat aagagagttg gtcttctcat aaatagtcac tagcttttctg
 301 atttttttc actttctata tcacgtaaat aggtactcaa atttgatatt tacaccaaac
 361 aaatgaaaat aggatatgtg ttttttcatac gtatatttat ctatcgtact taatgataca
 421 tacatataca tataaccttA cttttttgatt actaaaaatt taattatatt taatttgggt
 481 aaatatcaga tgccacaaaa catttaccta gccactgttt ttgactacta aaaatttaat
 541 tatgtttagc ttgggtaaat atcagatgc actaaacatt ttacctagcc attcctccga
 601 aaagaaattg agaaggaaat tagagttagt ggagccataa taatgtttaa tgtgaccata
 661 actcggtgaa aaccacggca agaataagaa acagctgtta aggctaacca acagctgcat
 721 atctttaagc catttgctat taccccaaca tcgcatcttc ctctgatccc gaccctacgg
 781 gcgtaaaaag tgtaaatcgt tagaattgtt ttatttatttt tatgatgtca ctatttttta
 841 aaatcaaaat taaattgggg tgtcgatttt tttgggtcct gcttatgtat agtatggcgc
 901 tatggaggca ctgagagagt ccgaaacgtt tctatataag gccaccccac gcattcacaa
 961 acttcgttcc caaacagaac aagaaaatca aatctcggag agagagagag agaaatattt
1021 tgagagagaa atacagaaaa tctctcttcc ttcttccttt tttttttcaa tccccattca
1081 tattcttttt ttagaataat ctatggcggc atctgtcgaa aacaggcagt tcagtcacct
1141 agaagccggt ttatccccggt ctttcaagcc ccggtctgat tccccggttc gtggctgcaa
1201 cttcccttcg cccaacagta ctaatttcca aaagaaacca aattccacca tttaccttga
1261 ttactcgtcg agtgagacg acgatgatga tgacgaaaaa aatgagtacc ttcaaatgat
1321 taaaaaaggg aattcagagt tagagccatc tgttcatgac actagggacg aaggtaccgc
1381 tgataattgg attgaacgca acttttccat gattcgtctc accggaaagc atccatttaa
1441 ctccgaacca ccgttgaacc ggctcatgca ccacggcttt atcacaccgg tcccacttca
1501 ttacgttcgt aaccatggac cggttcccaa gggcacgtgg gatgactgga ccgtggaagt
1561 cacgggacta gtgaagcgtc ctatgaaatt cacaatggac cagttggtta acgaattccc
1621 ttgtagagaa ttgcccgtta cgcttgtttg tgctggcaat cgaaggaaag aacagaacat
1681 ggttaaacaa accattggtt tcaactgggg cgccgctgcc gtttcaacaa cgatatggcg
1741 cggggtaccc ctccgcgctt tgctaaaacg gtgcggtgtt tttagcaaga ataaagggcc
1801 gcttaatgtt tgcttcgaag gagctgatgt gttgcccgga ggtggtggtt caaagtatgg
1861 aaccagcatt aagaaggaat ttgcaatgga tccagcacga gatatcatcg tagcctacat
1921 gcagaacgga gaaaaattgg cacccgacca cgggtttcca gtacgaatga taattccagg
1981 attcattgga ggaagaatgg tgaaatggat aaagaggatt atagtcacca cccaagaatc
2041 agacagctat tatcatttca aggacaatag agttcttcct ccccatgttg atgctgaact
2101 tgcaaatacc gaaggtacgt accgtaacta tttcaattta ttactccatt tgttccaatt
2161 tatgtgaacc tatttccttt ttggtccgtt caaaaaagaa tgaaccctttt ctaaatttgg
2221 taacaatttA gcttaaactt acaacttcac ccttaatgag aaactttttat aaccacacaa
2281 atacccctggg gcccatttgg acttgtttag gtcgacaaat tccaaaagtt ttatttttttt
2341 cttaaacttc gtgctcagtc aaacaggttc acgtaaattg aaacggagag agtatcattt
2401 ttattaaggg gtataaatat attttaatta gttgagactt gcacatacaa gtaaaatatt
2461 tcttagaata caaatcaac tgaaagctta cttctaatta tatggttttg aattttcctt
2521 tcaatgaagt aaataaaaag gaaacaatta tattcaacgc atgtaggtat atggtcctgt
2581 cattatctca aatcaaatgg tttaaagaca aaggactttg gaaacataga attgtcagct
2641 ttatagttat ggagtactat attagttagc tgtttgcatc tattcataat tggtctatct
2701 gtgtgcagca tggtggtaca agccagagta tatcatcaat gagcttaata ttaactctgt
2761 cattacgacg ccgtgtcatg aagaaatttt gccaattaac gcctggacga ctcagcgacc
2821 ttacacgttg aggggctatt cttattctgg ttagtatttt tatattttcc gattttgctg
```

SEQUENCE LISTING

```
2881 agaatatcat atttcttagt tttgtcgata catcgtatcc tctaactctg acgttttact
2941 tcgtccttat gcacccactt acgtccttac tttctcagac agtttattga tgaaaactac
3001 ttactatttt cgacccgata gcctcagcgt ccttaattaa atgtgatgtt ttgaaagaga
3061 tattctctcc cgtctatttt aattaatttt tggctgtttt tatacgtggg aatctatttt
3121 taacattaat taatatagaa atgaaccata ttaatattat taatttcttc attgaaaata
3181 caacaaatac tcttcggctc ttactacaat gacaattttg aagaaaaata attaattcct
3241 tcctaatatc tgaaaaatca aatattgtgg accataaaaa aaggtcaaaa aattaattaa
3301 aatgaactgg agagagtaaa ttagaaaata taattatagc actagtaatt aaagttatta
3361 gatgtcttct ttaaaaagcg tgtgaaaact ttaaagacga aatataatat gaatattatc
3421 taatacttag aaagtgtcaa taattggtag acaatttaaa ctatatacta gttaaaaagt
3481 ctgtcaatac aactattagt attggggatt agagagaata gtagtaaaat ggagtaattg
3541 gacgcatgag cttgggcatg ctgattgctg tcagcttgtt tgctaatgtg aaaaagaaaa
3601 tagtaagaaa aggccaacat ggttttgttt attttattat gtggtagtac acaaaaacct
3661 ggggagcttt cctagttctg aagagtcggt ctttggtagc acaaaattaa tagtatagta
3721 taccaagtga atattaaatt caattgtcta aagcacggaa tctttttgac tactttagtt
3781 cctgcatctt gggttgcctc aacaacaccc tttattgaat tattatagta atgttcaata
3841 taatatacaa ttagaaaaca ctctaagtgg tcactttata tggatctagt caatactatt
3901 tcttctaaac aacgtgccta attcttccc actttccagt acatgaccac cattaagttt
3961 aattttttgtc aattccttgt gcaattggcc cttcaaatga gcagaagtgt tacgtaggaa
4021 aactaacttc agctactatt ataggagtaa acctgttagg aaaagatgct cgaggaactg
4081 acaaaacttg tagaataatt agccattgta ttgattgaaa tactgattgt gaacgtgtaa
4141 caaacaggcg gagggaaaaa agtaacgcga gtagaagtga cgttggatgg aggagaaaca
4201 tggcaagtta gcacactaga tcacccagag aagcccacca aatatggcaa gtactggtgt
4261 tggtgctttt ggtcactcga ggttgaggtg ttagacttgc tcagtgctaa agaaattgct
4321 gttcgagctt gggatgagac cctcaatact caacccgaga agcttatttg gaacgtcatg
4381 gtacgttcac ttcttctttt acctttattt cttttaactt ctatatacta gcggtgtaaa
4441 gttatttttac accataagtt aacttacaaa aatatgtaac tatttatact acgagtgatg
4501 agggcaagaa ggggtttaag tatttgacaa taaatgtaaa ccctgcaatt ttgttcctaa
4561 ttttttatcc tttcaactct ttgtgattgc ttcattatct agattcacag agcacatgtg
4621 ttcacatgcc aaaacaaaaa actacaaaca aaaaaacttt tcactagctt tagtctaaga
4681 ttcccctttt ttttttttggg aggtgtgtgg tccatactcc atagatcaat tccagccact
4741 gacgtaccaa accctgaaaa ttcctagtag ttatagcgac gtacaatcat ttcatattat
4801 gtaagcagag acgtgatcac atgaactaga tgtgaatacc acttgcccag tccaccaggt
4861 caattcatct agatgtgtaa atcttgacac cagcactggg tcacttttat aacactagca
4921 tttaacaaca tttcatcctt gaacattact tgggctaatt aataagtatt tttttttata
4981 tactctaaaa attgtaatta cataaatgaa tttaacttat acacgctgac aatgttacta
5041 attccacttt ttacggacgg ttatctatag aaatcattta ggtgaaacaa ttctcttaca
5101 ctatgatcag tgttagtaca taatggttat tacatttttct aaatattgtg ctatgttgca
5161 atgttcaggg aatgatgaat aattgctggt tccgagtaaa gatgaatgtg tgcaagcctc
5221 acaagggaga gattggaata gtgtttgagc atccgactca acctggaaac caatcaggtg
5281 gatggatggc gaaggagaga catttggaga tatcagcaga ggcacctcaa acactaaaga
5341 agagtatctc aactccattc atgaacacag cttccaagat gtactccatg tccgaggtca
5401 ggaaacacag ctctgctgac tctgcttgga tcatagtcca tggtcatatc tatgacgcca
5461 cgcgttcttt gaaagatcac cctggtggga ctgacagcat tctcatcaat gctggcactg
5521 attgcactga ggaatttgat gcaattcatt ctgataaggc taagaagctc ttggaggatt
5581 tcaggattgg tgaactcata actactggtt acacctctga ctctcctggc aactccgtgc
5641 acggatcttc ttccttcagc agctttctag cacctattaa ggaacttgtt ccagcgcaga
5701 ggagtgtggc cctaattcca agagagaaaa tcccatgcaa actcatcgac aagcaatcca
5761 tctcccatga tgttaggaaa tttcgatttg cattgccctc tgaggatcaa gtcttgggct
5821 tgcctgttgg aaaacatatc ttcctctgtg ccgttattga cgataagctc tgcatgcgcg
5881 cttacacgcc tactagcacg atcgatgagg tggggtactt cgagttggtt gtcaagatat
5941 acttcaaagg aattcaccct aaattcccca atggagggca aatgtcacag tatcttgatt
6001 ctatgccgtt agggtcattt ctcgacgtga aggtccatt aggtcacatt gaataccaag
6061 gaaagggaaa tttcttagtt catggcaaac agaagtttgc caagaagttg gccatgatag
6121 caggtggaac aggaataact ccagtgtatc aagtcatgca ggcaattctg aaagatccag
6181 aagatgacac agaaatgtat gtggtgtatg ctaacagaac agaggatgat attttactta
6241 aggaagagct tgattcatgg gctgagaaaa ttccagaagg ggttaaagtt tggtatgtgg
6301 ttcaggattc tattaaagaa ggatggaagt acagcattgg ttttattaca gaagccattt
6361 tgagagaaca tatccctgag ccatctcaca caacactggc tttggcttgt ggaccacctc
6421 ctatgattca atttgctgtt aatccaaact tggagaagat gggctatgac attaaggatt
6481 ccttattggt gttctaattt taaaaacaaa acaatatctg caggaataaa tttttttttt
6541 cccctatca gttgtacata ttgtatttgg tttatcaccc ccatgtacta cgtagtgttt
6601 gtagttctta cattttatt ttttagaatt tttttaaacc ttaggatata aaggttttct
6661 cttccaacaa agtgattctt tagggaagaa atgtactgta ctgtactagt atgtctaagc
6721 cgaaagttgt aatgtttacc atgacaaatt gtattcaatt cctcatggaa tagtaacatt
6781 gtgttcatgt gtcttcctgt aagcgatctt caaaatatca atgtatatat atagtaattg
6841 caaaccattg ttcctttttcc cgatgtagtt aactactctt tctttagctt ctagtctctg
6901 gtgaatattt tttttttctat aactctttaa ttaatacggc cttaaataag agaaagtttt
6961 aaaccacgaa tatcattatg cagacgtata ggtaattaat ctacttttttg aaaaaaaatc
7021 tattttcttt atgtggtcct tcaaaataat attctagaac cttttgtata ttcccttta
7081 acttctattt agtttt
```

SEQUENCE LISTING

SEQ ID NO: 3 Mutant polypeptide sequence of *Nicotiana tabacum* NIA2 gene for nitrate reductase. The mutated polypeptide in the recognition site for binding of the nitrate reductase kinase is highlighted in bold and underline.

MAASVENRQFSHLEAGLSRSFKPRSDSPVRGCNFPSPNSTNFQKKPNSTIYLDYSSSEDDDDDDEKNEYL
QMIKKGNSELEPSVHDTRDEGTADNWIERNFSMIRLTGKHPENSEPPLNRLMHHGFITPVPLHYVRNHGP
VPKGTWDDWTVEVTGLVKRPMKFTMDQLVNEFPCRELPVTLVCAGNRRKEQNMVKQTIGFNWGAAAVSTT
IWRGVPLRALLKRCGVFSKNKGALNVCFEGADVLPGGGGSKYGTSIKKEFAMDPARDIIVAYMQNGEKLA
PDHGFPVRMIIPGFIGGRMVKWIKRIIVITQESDSYYHFKDNRVLPPHVDAELANTEAWWYKPEYIINEL
NINSVITTPCHEEILPINAWTTQRPYTLRGYSYSGGGKKVIRVEVTLDGGETWQVSTLDHPEKPIKYGKY
WCWCFWSLEVEVLDLLSAKEIAVRAWDETLNTQPEKLIWNVMGMMNNCWFRVKMNVCKPHKGEIGIVFEH
PTQPGNQSGGWMAKERHLEISAEAPQTLKKSISTPFINTASKMYSMSEVRKHSSADSAWIIVHGHIYDAT
RELKDHPGGIDSILINAGTDCTEEFDAIHSDKAKKLLEDFRIGELITTGYTSDSPGNSVHGSSSFSSFLA
PIKELVPAQRSVALIPREKIPCKLIDKQSISHDVRKFRFALPSEDQVLGLPVGKHIFLCAVIDDKLCMRA
YTPTSTIDEVGYFELVVKIYFKGIHPKFPNGGQMSQYLDSMPLGSFLDVKGPLGHIEYQGKGNELVHGKQ
KFAKKLAMIAGGIGITPVYQVMQAILKDPEDDTEMYVVYANRTEDDILLKEELDSWAEKIPERVKVWYVV
QDSIKEGWKYSIGFITEAILREHIPEPSHITLALACGPPPMIQFAVNPNLEKMGYDIKDSLLVF

SEQ ID NO: 4 Mutant polynucleotide sequence of *Nicotiana tabacum* NIA2 gene for nitrate reductase. The sequence which acts as the recognition site for binding of the nitrate reductase kinase responsible for the phosphorylation of NtNIA2 amino add S523 is highlighted in bold. The g to a mutation is underlined.

1 tacatacaag ggcgcgaata aacttttttt aaagtaaatg tatatgaact tgcaatgaaa
61 gaggacctta acttgtttgt ctttgttgct ttctgcaaat ttcaccttaa cagcccattt
121 gagattgatt tagttagtta taacaattag ttaaatgctt gtgtaatttg aagaaaatat
181 ttggacgtgc tcgctgaaaa cattatactc ctatataata gaaatacttt ctgaaaagtt
241 ggtcttgttc aaaaacgtat aagagagttg gtcttctcat aaatagtcac tagctttctg
301 atttttttc actttctata tcacgtaaat aggtactcaa atttgatatt tacaccaaac
361 aaatgaaaat aggatatgtg tttttcatac gtatatttat ctatcgtact taatgataca
421 tacatataca tataacctta ctttttgatt actaaaaatt taattatatt taatttgggt
481 aaatatcaga tgccacaaaa catttaccta gccactgttt ttgactacta aaaatttaat
541 tatgtttagc ttgggtaaat atcagatgtc actaaacatt ttacctagcc attcctccga
601 aaagaaattg agaaggaaat tagagttagt ggagccataa taatgtttaa tgtgaccata
661 actcggtgaa aaccacggca agaataagaa acagctgtta aggctaacca acagctgcat
721 atctttaagc catttgctat taccccaaca tcgcatcttc ctctgatccc gaccctacgg
781 gcgtaaaaag tgtaaatcgt tagaattgtt ttatttattt tatgatgtca ctattttta
841 aaatcaaaat taaattgggg tgtcgatttt tttgggtcct gcttatgtat agtatggcgc
901 tatggaggca ctgagagagt ccgaaacgtt tctatataag gccaccccac gcattcacaa
961 acttcgttcc caaacagaac aagaaaatca aatctcggag agagagagag agaaatattt
1021 tgagagagaa atacagaaaa tctctcttcc ttctttcctt tttttttcaa tccccattca
1081 tattcttttt ttagaataat ctatggcggc atctgtcgaa aacaggcagt tcagtcacct
1141 agaagccggt ttatcccggt ctttcaagcc ccggtctgat tccccggttc gtggctgcaa
1201 cttcccttcg cccaacagta ctaatttcca aaagaaacca aattccacca tttaccttga
1261 ttactcgtcg agtgaagacg acgatgatga tgacgaaaaa aatgagtacc ttcaaatgat
1321 taaaaaaggg aattcagagt tagagccatc tgttcatgac actagggacg aaggtaccgc
1381 tgataattgg attgaacgca acttttccat gattcgtctc accggaaagc atccatttaa
1441 ctccgaacca ccgttgaacc ggctcatgca ccacggcttt atcacaccgg tcccacttca
1501 ttacgttcgt aaccatggac cggttcccaa gggcacgtgg gatgactgga ccgtggaagt
1561 cacgggacta gtgaagcgtc ctatgaaatt cacaatggac cagttggtta acgaattccc
1621 ttgtagagaa ttgcccgtta cgcttgtttg tgctggcaat cgaaggaaag aacagaacat
1681 ggttaaacaa accattggtt tcaactgggg cgccgctgcc gtttcaacaa cgatatggcg
1741 cggggtaccc ctccgcgctt tgctaaaacg gtgcggtgtt tttagcaaga ataaaggggc
1801 gcttaatgtt tgcttcgaag gagctgatgt gttgcccgga ggtggtggtt caaagtatgg
1861 aaccagcatt aagaaggaat ttgcaatgga tccagcacga gatatcatcg tagcctacat
1921 gcagaacgga gaaaaattgg cacccgacca cgggtttcca gtacgaatga taattccagg
1981 attcattgga ggaagaatgg tgaaatggat aaagaggatt atagtcacca cccaagaatc
2041 agacagctat tatcatttca aggacaatag agttcttcct ccccatgttg atgctgaact
2101 tgcaaatacc gaaggtacgt accgtaacta tttcaattta ttactccatt tgttccaatt
2161 tatgtgaacc tatttccttt ttggtccgtt caaaaaagaa tgaacccttt ctaaatttgg
2221 taacaattta gcttaaactt acaacttcac ccttaatgag aaacttttat aaccacacaa
2281 ataccctggg gcccatttgg acttgtttag gtcgacaaat tccaaaagtt ttattttttt
2341 cttaaacttc gtgctcagtc aaacaggttc acgtaaattg aaacggagag agtatcattt
2401 ttattaaggg gtataaatat attttaatta gttgagactt gcacatacaa gtaaaatatt
2461 tcttagaata caaaatcaac tgaaagctta cttctaatta tatggttttg aattttcctt
2521 tcaatgaagt aaataaaaag gaaacaatta tattcaacgc atgtaggtat atggtcctgt
2581 cattatctca aatcaaatgg tttaaagaca aaggactttg gaaacataga attgtcagct
2641 ttatagttat ggagtactat attagttagc tgtttgcatc tattcataat tggtctatct
2701 gtgtgcagca tggtggtaca agccagagta tatcatcaat gagcttaata ttaactctgt
2761 cattacgacg ccgtgtcatg aagaaatttt gccaattaac gcctggacga ctcagcgacc
2821 ttacacgttg aggggctatt cttattctgg ttagtatttt tatattttcc gattttgctg
2881 agaatatcat atttcttagt tttgtcgata catcgtatcc tctaactctg acgttttact
2941 tcgtccttat gcacccactt acgtccttac tttctcagac agtttattga tgaaaactac
3001 ttactatttt cgacccgata gcctcagcgt ccttaattaa atgtgatgtt ttgaaagaga
3061 tattctctcc cgtctatttt aattaatttt tggctgtttt tatacgtggg aatctatttt
3121 taacattaat taatatagaa atgaaccata ttaatattat taatttcttc attgaaaata

```
3181 caacaaatac tcttcggctc ttactacaat gacaattttg aagaaaaata attaattcct
3241 tcctaatatc tgaaaaatca aatattgtgg accataaaaa aaggtcaaaa aattaattaa
3301 aatgaactgg agagagtaaa ttagaaaata taattatagc actagtaatt aaagttatta
3361 gatgtcttct ttaaaaagcg tgtgaaaact ttaaagacga aatataatat gaatattatc
3421 taatacttag aaagtgtcaa taattggtag acaatttaaa ctatatacta gttaaaaagt
3481 ctgtcaatac aactattagt attggggatt agagagaata gtagtaaaat ggagtaattg
3541 gacgcatgag cttgggcatg ctgattgctg tcagcttgtt tgctaatgtg aaaaagaaaa
3601 tagtaagaaa aggccaacat ggttttgttt atttattat gtggtagtac acaaaaacct
3661 ggggagcttt cctagttctg aagagtcggt ctttggtagc acaaaattaa tagtatagta
3721 taccaagtga atattaaatt caattgtcta aagcacggaa tcttttttgac tactttagtt
3781 cctgcatctt gggttgcctc aacaacaccc tttattgaat tattatagta atgttcaata
3841 taatatacaa ttagaaaaca ctctaagtgg tcactttata tggatctagt caatactatt
3901 tcttctaaac aacgtgccta attcttccc actttccagt acatgaccac cattaagttt
3961 aattttttgtc aattccttgt gcaattggcc ttcaaatga gcagaagtgt tacgtaggaa
4021 aactaacttc agctactatt aaaggagtaa acctgttagg aaaagatgct cgaggaactg
4081 acaaaacttg tagaataatt agccattgta ttgattgaaa tactgattgt gaacgtgtaa
4141 caaacaggcg gagggaaaaa agtaacgcga gtagaagtga cgttggatgg aggagaaaca
4201 tggcaagtta gcacactaga tcacccagag aagcccacca aatatggcaa gtactggtgt
4261 tggtgctttt ggtcactcga ggttgaggtg ttagacttgc tcagtgctaa agaaattgct
4321 gttcgagctt gggatgagac cctcaatact caacccgaga agcttatttg gaacgtcatg
4381 gtacgttcac ttcttctttt accttttattt cttttaactt ctatatacta gcggtgtaaa
4441 gttatttac accataagtt aacttacaaa aatatgtaac tatttatact acgagtgatg
4501 agggcaagaa ggggttaag tattgacaa taaatgtaaa ccctgcaatt ttgttcctaa
4561 ttttttatcc tttcaactct ttgtgattgc ttcattatct agattcacag agcacatgtg
4621 ttcacatgcc aaaacaaaaa actacaaaca aaaaaacttt tcactagctt tagtctaaga
4681 ttcccctttt ttttttttggg aggtgtgtgg tccatactcc atagatcaat tccagccact
4741 gacgtaccaa accctgaaaa ttcctagtag ttatagcgac gtacaatcat ttcatattat
4801 gtaagcagag acgtgatcac atgaactaga tgtgaatacc acttgcccag tccaccaggt
4861 caattcatct agatgtgtaa atcttgacac cagcactggg tcacttttat aacactagca
4921 tttaacaaca tttcatcctt gaacattact tgggctaatt aataagtatt tttttttata
4981 tactctaaaa attgtaatta cataaatgaa tttaacttat acacgctgac aatgttacta
5041 attccacttt ttacggacgg ttatctatag aaatcattta ggtgaaacaa ttctcttaca
5101 ctatgatcag tgttagtaca taatggttat tacattttct aaatattgtg ctatgttgca
5161 atgttcaggg aatgatgaat aattgctggt tccgagtaaa gatgaatgtg tgcaagcctc
5221 acaagggaga gattggaata gtgtttgagc atccgactca acctgaaac caatcaggtg
5281 gatggatggc gaaggagaga catttggaga tatcagcaga ggcacctcaa acactaaaga
5341 agagtatctc aactccattc ataaacacag cttccaagat gtactccatg tccgaggtca
5401 ggaaacacag ctctgctgac tctgcttgga tcatagtcca tggtcatatc tatgacgcca
5461 cgcgtttctt gaaagatcac cctggtggga ctgacagcat tctcatcaat gctggcactg
5521 attgcactga ggaatttgat gcaattcatt ctgataaggc taagaagctc ttggaggatt
5581 tcaggattgg tgaactcata actactggtt acacctctga ctctcctggg aactccgtgc
5641 acggatcttc ttccttcagc agctttctag cacctattaa ggaacttgtt ccagcgcaga
5701 ggagtgtggc cctaattcca agagagaaaa tcccatgcaa actcatcgac aagcaatcca
5761 tctcccatga tgttaggaaa tttcgatttg cattgccctc tgaggatcaa gtcttgggct
5821 tgcctgttga aaaacatatc ttcctctgtg ccgttattga cgataagctc tgcatgcgcg
5881 cttacacgcc tactagcaca atcgatgagg tggggtactt cgagttggtt gtcaagatat
5941 acttcaaagg aattcaccct aaattcccca atggagggca aatgtcacag tatcttgatt
6001 ctatgccgtt agggtcattt ctcgacgtga aaggtccatt aggtcacatt gaataccaag
6061 gaaagggaaa tttcttagtt catggcaaac agaagtttgc caagaagttg gccatgatag
6121 caggtggaac aggaataact ccagtgtatc aagtcatgca ggcaattctg aaagatccag
6181 aagatgacac agaaatgtat gtggtgtatg ctaacagaac agaggatgat attttactta
6241 aggaagagct tgattcatgg gctgagaaaa ttccagagag ggttaaagtt tggtatgtgg
6301 ttcaggattc tattaaagaa ggatggaagt acagcattgg ttttattaca gaagccattt
6361 tgagagaaca tatccctgag ccatctcaca caacactggc tttggcttgt ggaccacctc
6421 ctatgattca atttgctgtt aatccaaact tggagaagat gggctatgac attaaggatt
6481 ccttattggt gttctaattt taaaaacaaa acaatatctg caggaataaa tttttttttt
6541 ccccctatca gttgtacata ttgtatttgg tttatcaccc ccatgtacta cgtagtgttt
6601 gtagttctta cattttttatt tttttagaatt tttttaaacc ttaggatata aaggttttct
6661 cttccaacaa agtgattctt tagggaagaa atgtactgta ctgtactagt atgtctaagc
6721 cgaaagttgt aatgtttacc atgacaaatt gtattcaatt cctcatggaa tagtaacatt
6781 gtgttcatgt gtcttcctgt aagcgatctt caaaatatca atgtatatat atagtaattg
6841 caaaccattg ttccttttcc cgatgtagtt aactactctt tctttagctt ctagtctctg
6901 gtgaatattt ttttttctat aactctttaa ttaatacggc cttaaataag agaaaagttt
6961 aaaccacgaa tatcattatg cagacgtata ggtaattaat ctacttttttg aaaaaaaatc
7021 tattttcttt atgtggtcct tcaaaataat attctagaac cttttgtata ttcccttta
7081 acttctattt agtttt
```

SEQ ID NO: 5 Polypeptide sequence acting as the recognition site for binding of the nitrate reductase kinase responsible for the phosphorylation of NtNIA2 amino acid S523 from the wild type polypeptide sequence of Nicotiana tabacum NIA2 gene for nitrate reductase, GenBank Accession number X14059.
LK(K or R)(S or T)(I or V or A)S(T or S)PFM

SEQUENCE LISTING

SEQ ID NO: 6 Mutant polypeptide sequence of SEQ ID NO: 5.
LK(K or R)(S or T)(I or V or A)S(T or S)PFI SEQ ID NO: 7 Wild type polypeptide sequence acting as the recognition
site for binding of the nitrate reductase kinase responsible for the
phosphorylation of NtNIA2 amino acid S523 from the wild type poly-
peptide sequence of Nicotiana tabacum NIA2 gene for nitrate reductase,
GenBank Accession number X14059.
LKKSISTPFM SEQ ID NO: 8 (Mutant polypeptide sequence of SEQ ID NO: 7)..
LKKSISTPFI

TABLE 1

NtNIA2 M527I mutation details

| Mutant | Sequence before the mutation | Sequence after the mutation | Original codon | Original amino acid | Mutated codon | Mutated amino acid |
|---|---|---|---|---|---|---|
| M527I | Ctccattcat (SEQ ID NO: 9) | Aacacagctt (SEQ ID NO: 10) | atG | Met | atA | Ile |

The sequence information of the mutation NtNIA2 M527I is shown. The second and third columns show the 10 nucleotides immediately before the mutated nucleotide and the 10 nucleotides after the mutated nucleotide. The fourth and fifth columns report the original codon and amino acid (respectively) as in the wild type sequence. The last two columns report the codon and amino acid (respectively) in the mutated sequence. In bold and underlined is the G to A mutation.

TABLE 2

NtNIA2 specific primers details

| Primer | Sequence 5' to 3' |
|---|---|
| NIA2 forward | CCACTTTTTACGGACGGTTATCT (SEQ ID NO: 11) |
| NIA2 reverse | GCAAATCGAAATTTCCTAACATCAT (SEQ ID NO: 12) |

Reported are the sequence details of the NtNIA2 specific primers. The second column indicates the DNA sequences of the primers.

The invention claimed is:

1. A *Nicotiana tabacum* plant cell comprising:
a genome comprising a polynucleotide sequence encoding a nitrate reductase polypeptide comprising the polypeptide sequence of SEQ ID NO: 5 except that the methionine in SEQ ID NO: 5 is substituted for an amino acid that reduces nitrate levels in the plant cell as compared to a control *Nicotiana tabacum* plant cell, wherein the amino acid is glycine, alanine, proline, isoleucine, leucine, or valine,
wherein the *Nicotiana tabacum* plant cell is homozygous for the substitution to the amino acid.

2. The *Nicotiana tabacum* plant cell according to claim 1, wherein the methionine of SEQ ID NO: 5 is substituted for isoleucine.

3. The *Nicotiana tabacum* plant cell according to claim 1, wherein the nitrate reductase polypeptide comprises an amino acid substitution at a position corresponding to position 527 of a sequence having at least 80% sequence identity to SEQ ID NO: 1.

4. The *Nicotiana tabacum* plant cell according to claim 1, wherein the nitrate reductase polypeptide comprises or consists of the polypeptide sequence set forth in SEQ ID NO: 3.

5. The *Nicotiana tabacum* plant cell according to claim 1, wherein the polynucleotide sequence comprises or consists of a polynucleotide sequence having at least 80% sequence identity to SEQ ID NO: 4.

6. The *Nicotiana tabacum* plant cell according to claim 1, wherein the polynucleotide sequence comprises or consists of the polynucleotide sequence set forth in SEQ ID NO: 4.

7. The *Nicotiana tabacum* plant cell according to claim 1, wherein the *Nicotiana tabacum* plant cell is a *Nicotiana tabacum* plant cell from a *Nicotiana tabacum* AA37 cultivar.

8. A *Nicotiana tabacum* plant or part thereof comprising the *Nicotiana tabacum* plant cell according to claim 1.

9. *Nicotiana tabacum* plant material, cured *Nicotiana tabacum* plant material, or homogenized *Nicotiana tabacum* plant material comprising the *Nicotiana tabacum* plant cell according to claim 1.

10. A tobacco product comprising the *Nicotiana tabacum* plant cell of claim 1.

11. A method comprising the steps of:
(a) providing the *Nicotiana tabacum* plant cell according to claim 1; and
(b) propagating the *Nicotiana tabacum* plant cell into a *Nicotiana tabacum* plant.

12. A method for producing cured *Nicotiana tabacum* plant material with a reduced amount of nitrate as compared to control *Nicotiana tabacum* plant material, comprising the steps of:
(a) providing the *Nicotiana tabacum* plant or part thereof according to claim 8;
(b) harvesting the *Nicotiana tabacum* plant material from the plant or part thereof; and
(c) curing the *Nicotiana tabacum* plant material.

13. The method according to claim 12, wherein the curing method is selected from the group consisting of air curing, fire curing, smoke curing, and flue curing.

14. The *Nicotiana tabacum* plant cell according to claim 2, wherein the polypeptide comprises SEQ ID NO: 6 or SEQ ID NO: 8.

15. The *Nicotiana tabacum* plant or part thereof according to claim 8, wherein cured leaves of the *Nicotiana tabacum* plant or part thereof contain lower levels of nitrate as compared to a control *Nicotiana tabacum* plant or part thereof.

16. The *Nicotiana tabacum* plant material, cured *Nicotiana tabacum* plant material, or homogenized *Nicotiana tabacum* plant material of claim 9, wherein the cured *Nicotiana tabacum* plant material is air-cured or sun-cured or flue-cured *Nicotiana tabacum* plant material.

17. The *Nicotiana tabacum* plant material, cured *Nicotiana tabacum* plant material, or homogenized *Nicotiana tabacum* plant material of claim 9, wherein the *Nicotiana tabacum* plant material, cured *Nicotiana tabacum* plant material, or homogenized *Nicotiana tabacum* plant material comprises biomass, seed, stem, flowers, or leaves.

18. The *Nicotiana tabacum* plant cell according to claim 1, wherein the polypeptide sequence of SEQ ID NO: 5 comprises the polynucleotide sequence of SEQ ID NO: 7.

19. The *Nicotiana tabacum* plant cell according to claim 18, wherein the methionine of SEQ ID NO: 7 is substituted for isoleucine.

* * * * *